US009629528B2

(12) United States Patent
Woods et al.

(10) Patent No.: US 9,629,528 B2
(45) Date of Patent: Apr. 25, 2017

(54) IMAGING SYSTEM, METHOD AND DISTAL ATTACHMENT FOR MULTIDIRECTIONAL FIELD OF VIEW ENDOSCOPY

(71) Applicant: The General Hospital Corporation, Boston, MA (US)

(72) Inventors: Kevin Woods, Atlanta, GA (US); Brett Eugene Bouma, Qunicy, MA (US); Guillermo J. Tearney, Cambridge, MA (US); Dongkyun Kang, Somerville, MA (US); Tao Wu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 151 days.

(21) Appl. No.: 14/389,631

(22) PCT Filed: Mar. 15, 2013

(86) PCT No.: PCT/US2013/031948
§ 371 (c)(1),
(2) Date: Sep. 30, 2014

(87) PCT Pub. No.: WO2013/148306
PCT Pub. Date: Oct. 3, 2013

(65) Prior Publication Data
US 2015/0073210 A1 Mar. 12, 2015

Related U.S. Application Data

(60) Provisional application No. 61/618,225, filed on Mar. 30, 2012.

(51) Int. Cl.
*A61B 1/00* (2006.01)
*A61B 1/06* (2006.01)
(Continued)

(52) U.S. Cl.
CPC ........ *A61B 1/0638* (2013.01); *A61B 1/00096* (2013.01); *A61B 1/00101* (2013.01);
(Continued)

(58) Field of Classification Search
CPC . A61B 1/0638; A61B 1/0661; A61B 1/00137; A61B 1/018; A61B 1/015
(Continued)

(56) References Cited

U.S. PATENT DOCUMENTS 2,339,754 A 1/1944 Brace
3,090,753 A 5/1963 Matuszak et al.
(Continued)

FOREIGN PATENT DOCUMENTS

CN 1550203 12/2004
DE 4105221 9/1991
(Continued)

OTHER PUBLICATIONS

Office Action dated Jan. 25, 2010 for U.S. Appl. No. 11/537,048.
(Continued)

Primary Examiner — Timothy J Neal
(74) Attorney, Agent, or Firm — Andrews Kurth Kenyon LLP

(57) ABSTRACT

An exemplary apparatus for imaging at least one anatomical structure can be provided. For example, the apparatus can include an endoscopic first arrangement, a radiation source second arrangement which provides at least one electro-magnetic radiation, and a third arrangement attached to at least one portion of the endoscopic arrangement. The third arrangement can contain an optical arrangement which, upon impact by the at least one electro-magnetic radiation and based thereon, may transmit a first radiation and reflects a second radiation. The first radiation can impact at least one first portion of the anatomical structure(s), and the second
(Continued)

radiation can impact at least one second portion of the anatomical structure(s). The first and second portions can be at least partially different from one another. Further, the first and second radiations can have characteristics which are different from one another.

11 Claims, 10 Drawing Sheets

(51) Int. Cl.
    *A61B 1/015*     (2006.01)
    *A61B 1/018*     (2006.01)

(52) U.S. Cl.
    CPC ...... *A61B 1/00137* (2013.01); *A61B 1/00181* (2013.01); *A61B 1/015* (2013.01); *A61B 1/018* (2013.01); *A61B 1/0661* (2013.01)

(58) Field of Classification Search
    USPC ........................................ 600/104, 178, 153
    See application file for complete search history.

(56) References Cited

U.S. PATENT DOCUMENTS

| | | |
|---|---|---|
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano et al. |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefèvre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,177,488 A | 1/1993 | Wang et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,257,617 A * | 11/1993 | Takahashi .......... A61B 1/00142 600/123 |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,400,771 A | 3/1995 | Pirak et al. |
| 5,404,415 A | 4/1995 | Mori et al. |
| 5,411,016 A | 5/1995 | Kume et al. |
| 5,414,509 A | 5/1995 | Veligdan |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,479,928 A | 1/1996 | Cathignol et al. |
| 5,486,701 A | 1/1996 | Norton et al. |
| 5,491,524 A | 2/1996 | Hellmuth et al. |
| 5,491,552 A | 2/1996 | Knuttel |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knuttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab |
| 5,628,313 A | 5/1997 | Webster, Jr. |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,701,155 A | 12/1997 | Wood et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |

(56) References Cited

U.S. PATENT DOCUMENTS

| | | |
|---|---|---|
| 5,740,808 A | 4/1998 | Panescu et al. |
| 5,748,318 A | 5/1998 | Maris et al. |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Baker et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory et al. |
| 5,829,439 A | 11/1998 | Yokosawa et al. |
| 5,836,877 A | 11/1998 | Zavislan et al. |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,052,186 A | 4/2000 | Tsai |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochmann et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | Harris et al. |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |

(56) References Cited

U.S. PATENT DOCUMENTS

| | | |
|---|---|---|
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,355 B2 | 5/2004 | Drabarek |
| 6,741,884 B1 | 5/2004 | Freeman et al. |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,145,661 B2 | 12/2006 | Hitzenberger |
| 7,148,970 B2 | 12/2006 | De Boer |
| 7,158,234 B2 * | 1/2007 | Uchiyama ............ A61B 1/0008 356/479 |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Guillermo et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,365,858 B2 | 4/2008 | Fang-Yen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,799,558 B1 | 9/2010 | Dultz |
| 7,805,034 B2 | 9/2010 | Kato et al. |
| 7,817,354 B2 * | 10/2010 | Wilson ................ A61B 1/041 359/725 |
| 7,911,621 B2 | 3/2011 | Motaghiannezam et al. |
| 7,969,578 B2 | 6/2011 | Yun et al. |
| 7,973,936 B2 | 7/2011 | Dantus |
| 8,315,282 B2 | 11/2012 | Huber et al. |
| 2001/0020126 A1 | 9/2001 | Swanson et al. |
| 2001/0036002 A1 | 11/2001 | Tearney et al. |
| 2001/0047137 A1 | 11/2001 | Moreno et al. |
| 2001/0055462 A1 | 12/2001 | Seibel |
| 2002/0016533 A1 | 2/2002 | Marchitto et al. |
| 2002/0024015 A1 | 2/2002 | Hoffmann et al. |
| 2002/0037252 A1 | 3/2002 | Toida et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Roche et al. |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0166946 A1 | 11/2002 | Iizuka et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0025917 A1 | 2/2003 | Suhami |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0103212 A1 | 6/2003 | Westphal et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0191392 A1 | 10/2003 | Haldeman |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039252 A1 | 2/2004 | Koch |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |

(56) References Cited

U.S. PATENT DOCUMENTS

| | | |
|---|---|---|
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0188148 A1 | 9/2004 | Chen et al. |
| 2004/0189999 A1 | 9/2004 | De Groot et al. |
| 2004/0204651 A1 | 10/2004 | Freeman et al. |
| 2004/0212808 A1 | 10/2004 | Okawa et al. |
| 2004/0239938 A1 | 12/2004 | Izatt et al. |
| 2004/0246490 A1 | 12/2004 | Wang |
| 2004/0246583 A1 | 12/2004 | Mueller et al. |
| 2004/0247268 A1 | 12/2004 | Ishihara et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0049488 A1 | 3/2005 | Homan |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Wallace et al. |
| 2005/0221270 A1 | 10/2005 | Connelly et al. |
| 2005/0254059 A1 | 11/2005 | Alphonse |
| 2005/0254061 A1 | 11/2005 | Alphonse et al. |
| 2006/0020172 A1 | 1/2006 | Luerssen et al. |
| 2006/0033923 A1 | 2/2006 | Hirasawa et al. |
| 2006/0039004 A1 | 2/2006 | De Boer et al. |
| 2006/0051036 A1 | 3/2006 | Treado |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Bernstein et al. |
| 2006/0171503 A1 | 8/2006 | O'Hara et al. |
| 2006/0184048 A1 | 8/2006 | Saadat et al. |
| 2006/0189928 A1 | 8/2006 | Camus et al. |
| 2006/0193352 A1 | 8/2006 | Chong et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0024860 A1 | 2/2007 | Tobiason et al. |
| 2007/0035743 A1 | 2/2007 | Vakoc et al. |
| 2007/0038040 A1 | 2/2007 | Cense et al. |
| 2007/0048818 A1 | 3/2007 | Rosen et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0203404 A1 | 8/2007 | Zysk et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0238955 A1 | 10/2007 | Tearney et al. |
| 2007/0253901 A1 | 11/2007 | Deng et al. |
| 2007/0258094 A1 | 11/2007 | Izatt et al. |
| 2007/0263226 A1 | 11/2007 | Kurtz et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0013960 A1 | 1/2008 | Tearney et al. |
| 2008/0021275 A1 | 1/2008 | Tearney et al. |
| 2008/0049220 A1 | 2/2008 | Izzia et al. |
| 2008/0070323 A1 | 3/2008 | Hess et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0139906 A1 | 6/2008 | Bussek |
| 2008/0152353 A1 | 6/2008 | de Boer et al. |
| 2008/0154090 A1 | 6/2008 | Hashimshony |
| 2008/0192236 A1 | 8/2008 | Smith et al. |
| 2008/0201081 A1 | 8/2008 | Reid |
| 2008/0204762 A1 | 8/2008 | Izatt et al. |
| 2008/0218696 A1 | 9/2008 | Mir |
| 2008/0226029 A1 | 9/2008 | Weir et al. |
| 2008/0228086 A1 | 9/2008 | Ilegbusi |
| 2008/0234560 A1 | 9/2008 | Nomoto et al. |
| 2008/0252901 A1 | 10/2008 | Shimizu |
| 2008/0265130 A1 | 10/2008 | Colomb et al. |
| 2008/0267562 A1* | 10/2008 | Wang ............... A61B 5/0062 385/31 |
| 2008/0297806 A1 | 12/2008 | Motaghiannezam |
| 2008/0308730 A1 | 12/2008 | Vizi et al. |
| 2009/0004453 A1 | 1/2009 | Murai et al. |
| 2009/0005691 A1 | 1/2009 | Huang |
| 2009/0011948 A1 | 1/2009 | Uniu et al. |
| 2009/0012368 A1 | 1/2009 | Banik et al. |
| 2009/0044799 A1 | 2/2009 | Qiu |
| 2009/0051923 A1 | 2/2009 | Zuluaga |
| 2009/0131801 A1 | 5/2009 | Suter et al. |
| 2009/0192358 A1 | 7/2009 | Jaffer et al. |
| 2009/0196477 A1 | 8/2009 | Cense et al. |
| 2009/0209834 A1 | 8/2009 | Fine |
| 2009/0273777 A1 | 11/2009 | Yun et al. |
| 2009/0281390 A1 | 11/2009 | Qiu et al. |
| 2009/0290156 A1 | 11/2009 | Popescu et al. |
| 2009/0305309 A1 | 12/2009 | Chien et al. |
| 2009/0306520 A1 | 12/2009 | Schmitt et al. |
| 2009/0323056 A1 | 12/2009 | Yun et al. |
| 2010/0002241 A1 | 1/2010 | Hirose |
| 2010/0053312 A1* | 3/2010 | Watanabe ......... A61B 1/00096 348/65 |
| 2010/0081873 A1* | 4/2010 | Tanimura .......... A61B 1/00096 600/109 |
| 2010/0086251 A1 | 4/2010 | Xu et al. |
| 2010/0094576 A1 | 4/2010 | de Boer et al. |
| 2010/0145145 A1 | 6/2010 | Shi et al. |
| 2010/0150467 A1 | 6/2010 | Zhao et al. |
| 2010/0261995 A1 | 10/2010 | Mckenna et al. |
| 2010/0309477 A1 | 12/2010 | Yun et al. |
| 2011/0028967 A1 | 2/2011 | Rollins et al. |
| 2011/0160681 A1 | 6/2011 | Dacey, Jr. et al. |
| 2011/0218403 A1 | 9/2011 | Tearney et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| DE | 102005034443 | 2/2007 |
| EP | 0029555 A2 | 6/1981 |
| EP | 0110201 | 6/1984 |
| EP | 0251062 | 1/1988 |
| EP | 0617286 | 2/1994 |
| EP | 0590268 | 4/1994 |
| EP | 0697611 | 2/1996 |
| EP | 0728440 | 8/1996 |
| EP | 0933096 | 8/1999 |

(56) References Cited

FOREIGN PATENT DOCUMENTS

| | | |
|---|---|---|
| EP | 1324051 | 7/2003 |
| EP | 1426799 | 6/2004 |
| EP | 2149776 | 2/2010 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 361040633 | 3/1986 |
| JP | 62-188001 | 6/1989 |
| JP | 04-056907 | 2/1992 |
| JP | 20040056907 | 2/1992 |
| JP | 4135550 | 5/1992 |
| JP | 4135551 | 5/1992 |
| JP | 5509417 | 11/1993 |
| JP | 8-136345 | 5/1996 |
| JP | H08-160129 | 6/1996 |
| JP | 9-10213 | 1/1997 |
| JP | 9-230248 | 9/1997 |
| JP | 10-213485 | 8/1998 |
| JP | 10-267631 | 10/1998 |
| JP | 10-267830 | 10/1998 |
| JP | 2259617 | 10/1999 |
| JP | 2000-023978 | 1/2000 |
| JP | 2000-046729 | 2/2000 |
| JP | 2000-121961 | 4/2000 |
| JP | 2000-504234 | 4/2000 |
| JP | 2000-126116 | 5/2000 |
| JP | 2000-131222 | 5/2000 |
| JP | 2001-4447 | 1/2001 |
| JP | 2001-500026 | 1/2001 |
| JP | 2001-104315 | 4/2001 |
| JP | 2001-174404 | 6/2001 |
| JP | 2001-174744 | 6/2001 |
| JP | 2001-507251 | 6/2001 |
| JP | 2001-508340 | 6/2001 |
| JP | 2007-539336 | 6/2001 |
| JP | 2001-212086 | 8/2001 |
| JP | 2008-533712 | 8/2001 |
| JP | 2001-264246 | 9/2001 |
| JP | 2001-515382 | 9/2001 |
| JP | 2001-525580 | 12/2001 |
| JP | 2002-503134 | 1/2002 |
| JP | 2002-035005 | 2/2002 |
| JP | 2002-205434 | 2/2002 |
| JP | 2002-095663 | 4/2002 |
| JP | 2002-113017 | 4/2002 |
| JP | 2002-148185 | 5/2002 |
| JP | 2002-516586 | 6/2002 |
| JP | 2002-214127 | 7/2002 |
| JP | 2002-214128 | 7/2002 |
| JP | 2002214127 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2004-028970 | 1/2004 |
| JP | 2004-037165 | 2/2004 |
| JP | 2004-057652 | 2/2004 |
| JP | 2004-089552 | 3/2004 |
| JP | 2004-113780 | 4/2004 |
| JP | 2004-514920 | 5/2004 |
| JP | 2004-258144 | 9/2004 |
| JP | 2004-317437 | 11/2004 |
| JP | 2005-062850 | 3/2005 |
| JP | 2005-110208 | 4/2005 |
| JP | 2005-510323 | 4/2005 |
| JP | 2005-156540 | 6/2005 |
| JP | 2005-516187 | 6/2005 |
| JP | 2005-195485 | 7/2005 |
| JP | 2005-241872 | 9/2005 |
| JP | 2006-237359 | 9/2006 |
| JP | 2007-500059 | 1/2007 |
| JP | 2007-075403 | 3/2007 |
| JP | 2007-83053 | 4/2007 |
| JP | 2007-524455 | 8/2007 |
| JP | 2007271761 | 10/2007 |
| JP | 2003-102672 | 4/2012 |
| RU | 2149464 | 5/2000 |
| RU | 2209094 | 7/2003 |
| RU | 2213421 | 9/2003 |
| RU | 2242710 | 12/2004 |
| RU | 2255426 | 6/2005 |
| RU | 2108122 | 6/2006 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 96-02184 | 2/1996 |
| WO | 96-04839 | 2/1996 |
| WO | 9628212 | 9/1996 |
| WO | 9732182 | 9/1997 |
| WO | 9800057 | 1/1998 |
| WO | 9801074 | 1/1998 |
| WO | 9818132 | 4/1998 |
| WO | 98-35203 | 8/1998 |
| WO | 9835203 | 8/1998 |
| WO | 9838907 | 9/1998 |
| WO | 9849123 | 10/1998 |
| WO | 9848838 | 11/1998 |
| WO | 9848846 | 11/1998 |
| WO | 9905487 | 2/1999 |
| WO | 9944089 | 2/1999 |
| WO | 99-28856 | 6/1999 |
| WO | 99-45838 | 9/1999 |
| WO | 9944089 | 9/1999 |
| WO | 1999-45338 | 10/1999 |
| WO | 9957507 | 11/1999 |
| WO | 00-43730 | 7/2000 |
| WO | 2000-42906 | 7/2000 |
| WO | 0058766 | 10/2000 |
| WO | 01-04828 | 1/2001 |
| WO | 0101111 | 1/2001 |
| WO | 0108579 | 2/2001 |
| WO | 0127679 | 4/2001 |
| WO | 01-33215 | 5/2001 |
| WO | 01-38820 | 5/2001 |
| WO | 0138820 | 5/2001 |
| WO | 01-42735 | 6/2001 |
| WO | 0142735 | 6/2001 |
| WO | 01-82786 | 11/2001 |
| WO | 02-37075 | 5/2002 |
| WO | 0236015 | 5/2002 |
| WO | 0238040 | 5/2002 |
| WO | 02037075 | 5/2002 |
| WO | 02-45572 | 6/2002 |
| WO | 02-068853 | 6/2002 |
| WO | 02-054027 | 7/2002 |
| WO | 0253050 | 7/2002 |
| WO | 02054027 | 7/2002 |
| WO | 2002-083003 | 10/2002 |
| WO | 02084263 | 10/2002 |
| WO | 03-003903 | 1/2003 |
| WO | 03-013624 | 2/2003 |
| WO | 2003-012405 | 2/2003 |
| WO | 03013624 | 2/2003 |
| WO | 03020119 | 3/2003 |
| WO | 03046495 | 6/2003 |
| WO | 03046636 | 6/2003 |
| WO | 03052478 | 6/2003 |
| WO | 03053226 | 7/2003 |
| WO | 03062802 | 7/2003 |
| WO | 03-088826 | 10/2003 |
| WO | 03105678 | 12/2003 |
| WO | 2004034869 | 4/2004 |
| WO | 2004-037068 | 5/2004 |
| WO | 2004-043251 | 5/2004 |
| WO | 2004057266 | 7/2004 |

(56) References Cited

FOREIGN PATENT DOCUMENTS

| WO | 2004066824 | 8/2004 |
|---|---|---|
| WO | 2004-073501 | 9/2004 |
| WO | 2004088361 | 10/2004 |
| WO | 2004-100789 | 11/2004 |
| WO | 2004-105598 | 12/2004 |
| WO | 2004105598 | 12/2004 |
| WO | 2005000115 | 1/2005 |
| WO | 2005-045362 | 5/2005 |
| WO | 2005-047813 | 5/2005 |
| WO | 2005047813 | 5/2005 |
| WO | 2005054780 | 6/2005 |
| WO | 2005082225 | 9/2005 |
| WO | 20050082225 | 9/2005 |
| WO | 2006004743 | 1/2006 |
| WO | 2006-020605 | 2/2006 |
| WO | 2006014392 | 2/2006 |
| WO | 2006039091 | 4/2006 |
| WO | 20060038876 | 4/2006 |
| WO | 2006-050320 | 5/2006 |
| WO | 2006-058187 | 6/2006 |
| WO | 2006059109 | 6/2006 |
| WO | 2006124860 | 11/2006 |
| WO | 2006-131859 | 12/2006 |
| WO | 2006130797 | 12/2006 |
| WO | 2007-030835 | 3/2007 |
| WO | 2007028531 | 3/2007 |
| WO | 2007038787 | 4/2007 |
| WO | 2007083138 | 7/2007 |
| WO | 2007084995 | 7/2007 |
| WO | WO 2008/134449 A1 | 11/2008 |
| WO | WO 2008/151287 | 12/2008 |
| WO | 2009-033064 | 3/2009 |
| WO | 2009153929 | 12/2009 |
| WO | 2011-055376 | 5/2011 |
| WO | 2011-080713 | 7/2011 |

OTHER PUBLICATIONS

International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414.564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese Office Action dated Aug. 4, 2010 for CN 200780005949.9.
Chinese Office Action dated Aug. 4, 2010 for CN 200780016266.3.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
European Search Report dated Dec. 3, 2010 for EP 10182442.3.
Notice of Reasons for Rejection dated May 5, 2010 for JP 2006-515266.
Office Action dated Jun. 4, 2010 for U.S. Appl. No. 11/285,301.
Office Action dated Jun. 8, 2010 for U.S. Appl. No. 12/201,816.
Chinese Office Action dated Jun. 8, 2010 for Chinese application No. 200780031332.4.
Office Action dated Jun. 10, 2010 for U.S. Appl. No. 11/505,700.
European Office Action dated Jun. 11, 2010 for EP 07761877.5.
European Office Action dated Jul. 14, 2010 for EP 06751266.5.
Office Action dated Sep. 29, 2010 for U.S. Appl. No. 11/672,571.
International Search Report and Written Opinion dated Aug. 31, 2010 for PCT/US2010/022034.
Office Action dated Oct. 20, 2010 for U.S. Appl. No. 12/015,642.
Office Action dated Oct. 25, 2010 for U.S. Appl. No. 11/622,854.
Office Action dated Oct. 26, 2010 for U.S. Appl. No. 11/211,482.
Office Action dated Oct. 27, 2010 for U.S. Appl. No. 11/744,287.
Office Action dated Nov. 15, 2010 for U.S. Appl. No. 12/795,529.
Notice of Allowance and Fees mailed Nov. 23, 2010 for U.S. Appl. No. 12/627,918.
Office Action dated Nov. 24, 2010 for U.S. Appl. No. 11/624,334.
Notice of Allowance and Fees mailed Dec. 1, 2010 for U.S. Appl. No. 12/261,967.
Office Action mailed Dec. 3, 2010 for U.S. Appl. No. 12/210,979.
International Search Report and Written Opinion dated Feb. 23, 2011 for PCT/US2010/041923.
Extended European Search Report mailed Dec. 14, 2010 for EP 10182301.1.
International Search Report dated Apr. 29, 2011 for PCT/US2010/051715.
International Search report dated Sep. 13, 2010 for PCT/US2010/023215.
International Search report dated Jul. 28, 2011 for PCT/US2010/059534.
International Search report dated Nov. 18, 2011 for PCT/US2011/027450.
International Search report dated Nov. 18, 2011 for PCT/US2011/027437.
International Search report dated Nov. 22, 2011 for PCT/US2011/027421.
Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia-Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.

(56) References Cited

OTHER PUBLICATIONS

Seltzer et al., (1991) "160 nm Continuous Tuning of a MQW Laser in an External Cavity Across the Entire 1.3 μm Communications Window," Electronics Letters, vol. 27, pp. 95-96.
Office Action dated Apr. 8, 2010 of U.S. Appl. No. 11/414,564.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Zhang et al., "Full Range Polarization-Sensitive Fourier Domain Optical Coherence Tomography" Optics Express, Nov. 29, 2004, vol. 12, No. 24.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interference Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al. "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Wide-field fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).
Feng et al., "Mesocopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
The Supplemental European Search Report for European Patent Application No. 13768632 mailed on Oct. 30, 2015.
Office Action dated Oct. 1, 2008 for U.S. Appl. No. 11/955,986.
Invitation to Pay Additional Fees dated Aug. 7, 2008 for International Application No. PCT/US2008/062354.
Invitation to Pay Additional Fees dated Jul. 29, 2008 for International Application No. PCT/US20074/081982.
International Search Report and Written Opinion dated Mar. 7, 2006 for International Search Report for PCT/US2005/035711.
International Search Report and Written Opinion dated Jul. 18, 2008 for International Application No. PCT/US2008/05733.
International Search Report and Written Opinion dated Jul. 4, 2008 for International Application No. PCT/US2008/051432.
Office Action dated Jun. 30, 2008 for U.S. Appl. No. 11/670,058.
Office Action dated Jul. 7, 2008 for U.S. Appl. No. 10/551,735.
Australian Examiners Report dated May 27, 2008 for Australian Patent Application No. 2003210669.
Notice of Allowance mailed Jun. 4, 2008 for U.S. Appl. No. 11/174,425.
European Communication dated May 15, 2008 for European patent application No. 05819917.5.
International Search Report and Written Opinion dated Jun. 10, 2008 for International Application No. PCT/US2008/051335.
Office Action dated Aug. 21, 2008 for U.S. Appl. No. 11/505,700.
International Search Report and Written Opinion dated Jul. 17, 2008 for International Application No. PCT/US2008/057450.
International Search Report and Written Opinion dated Aug. 11, 2008 for International Application No. PCT/US2008/058703.
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 25, 2008 for U.S. Appl. No. 09/709,162.
Office Action dated Aug. 21, 2008 for U.S. Appl. No. 11/956,079.
International Search Report and Written Opinion dated Oct. 9, 2008 for International Application No. PCT/US2008/081982.
International Search Report and Written Opinion dated Aug. 27, 2008 for International Application No. PCT/US2008/060600.
International Search Report and Written Opinion dated Aug. 7, 2008 for International Application No. PCT/US2007/074873.
International Search Report and Written Opinion dated Feb. 5, 2007 for International Application No. PCT/US2006/031275.
International Search Report and Written Opinion dated Mar. 23, 2006 for International Application No. PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
International Search Report and Written Opinion dated Feb. 2, 2009 for International Application No. PCT/US2008/071786.
International Search Report and Written Opinion dated Jan. 15, 2009 for International Application No. PCT/US2008/074863.
Office Action dated Feb. 17, 2009 for U.S. Appl. No. 11/211,483.

(56) References Cited

OTHER PUBLICATIONS

Japanese Office Action dated Dec. 2, 2008.
International Search Report and Written Opinion dated Feb. 24, 2009 for PCT/US2008/076447.
European Official Communication dated Feb. 12, 2008 for EP 07718117.0.
International Search Report and Written Opinion dated Jun. 10, 2009 for PCT/US2008/075456.
European Search Report issued May 5, 2009 for European Application No. 01991471.2.
Notice of Reasons for Reject dated Jul. 14, 2009 for Japanese Application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
International Search Report and Written Opinion dated Dec. 23, 2009.
Office Action Dated Dec. 9, 2008 for U.S. Appl. No. 09/709,162.
Office Action dated Dec. 23, 2008 for U.S. Appl. No. 11/780,261.
Office Action dated Jan. 9, 2009 for U.S. Appl. No. 11/624,455.
Office Action dated Feb. 18, 2009 for U.S. Appl. No. 11/285,301.
Office Action dated Feb. 18, 2009 for U.S. Appl. No. 11/697,012.
Office Action dated Feb. 23, 2009 for U.S. Appl. No. 11/956,129.
Office Action dated Mar. 16, 2009 for U.S. Appl. No. 11/621,694.
Office Action dated Mar. 24, 2009 for U.S. Appl. No. 11/744,412.
Office Action dated Oct. 1, 2009 for U.S. Appl. No. 11/677,278.
Office Action dated Oct. 6, 2009 for U.S. Appl. No. 12/015,642.
Summons to attend Oral Proceedings for European Patent No. 06813365.1 dated Oct. 9, 2009.
Office Action dated Dec. 14, 2009 for U.S. Appl. No. 11/537,123.
Office Action dated Dec. 15, 2009 for U.S. Appl. No. 11/549,397.
Liptak David C. et al., (2007) "On the Development of a Confocal Rayleigh-Brillouin Microscope" *American Institute of Physics* vol. 78, 016106.
Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer for Optical Coherence Tomography (OCT) Application" Optics Communications vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Australian Examiner's Report mailed May 27, 2008 for Australian patent application No. 2003210669.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.

Sticker, Markus (2002) En Face Imaging of Single Cell layers by Differential Phase-Contrast Optical Coherence Microscopy) *Optics Letters*, Col. 27, No. 13, Jul. 1, 2002.
US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
Notice of Reasons for Rejection mailed Dec. 2, 2008 for Japanese patent application No. 2000-533782.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.

(56) References Cited

OTHER PUBLICATIONS

Japanese Notice of Reasons for Rejection dated Jul. 14, 2009 for Japanese Patent application No. 2006-503161.
Office Action dated Jan. 9, 2010 for U.S. Appl. No. 11/624,455.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Zhang et al, (Sep. 2004), "Fourier Domain Functional Optical Coherence Tomography", Saratov Fall Meeting 2004, pp. 8-14.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
International Search Report for International Patent Application No. PCT/US2013/031948 mailed on Jul. 11, 2013.
International Written Opinion for International Patent Application No. PCT/US2013/031948 mailed on Jul. 11, 2013.
Winawer SJ, et al. Prevention of colorectal cancer by colonoscopic polypectomy. The National Polyp Study Workgroup. N Engl J Med 1993;329:1977-81.
Bressler B, et al. Colonoscopic miss rates for right-sided colon cancer: a population-based analysis. Gastroenterology 2004;127:452-6.
Rex DK, et al. Colonoscopic miss rates of adenomas determined by back-to-back colonoscopies. Gastroenterology 1997;112:24-8.
Haseman JH, et al., Failure of colonoscopy to detect colorectal cancer: evaluation of 47 cases in 20 hospitals. Gastrointest Endosc 1997;45:451-5.
Pellise M, et al. Impact of wide-angle, high-definition endoscopy in the diagnosis of colorectal neoplasia: a randomized controlled trial. Gastroenterology 2008;135:1062-8.
Rex DK, et al. Wide angle colonoscopy with a prototype instrument: impact on miss rates and efficiency as determined by back-to-back colonoscopies. Am J Gastr 2003;98:2000-5.
Deenadayalu VP,et al 170 degrees wide-angle colonoscope: effect on efficiency and miss rates. Am J Gastroenterol 2004;99:2138-42.
Matsushita et al. Efficacy of total colonoscopy with a transparent cap in comparison with colonoscopy without the cap. Endoscopy 1998;30:444-7.
Lee YT, et al. Improved colonoscopy success rate with a distally attached mucosectomy cap. Endoscopy 2006;38:739-42.
Kondo S, et al A randomized controlled trial evaluating the usefulness of a transparent hood attached to the tip of the colonoscope. Am J Gastroenterol 2007;102:75-81.
Harada Y, et al. Impact of a transparent hood on the performance of total colonoscopy: a randomized controlled trial. Gastrointest Endosc 2009;69:637-44.
Horiuchi A, Nakayama Y. Improved colorectal adenoma detection with a transparent retractable extension device. Am J Gastroenterol 2008;103:341-5.
Hewett DG, Rex DK. Cap-fitted colonoscopy: a randomized, tandem colonoscopy study of adenoma miss rates. Gastrointest Endosc 2010;72:775-81.
Triadafilopoulos G, et al A novel retrograde-viewing auxiliary imaging device (Third Eye Retroscope) improves the detection . . . colon. Gastrointest Endosc 2007; 65:139-44.
Leufkens AM, et al Effect of a retrograde-viewing device on adenoma detection rate during colonoscopy: the TERRACE study. Gastrointest Endosc 2011;73:480-9.
U.S. equivalent is provided.
International Search Report dated Jun. 1, 2006 PCT/US2005/043951.
Japanese Patent Application No. 2002-538830 dated May 12, 2008.
Office Action dated Aug. 24, 2006 for U.S. Appl. No. 10/137,749.
Office Action dated Nov. 13, 2006 for U.S. Appl. No. 10/501,268.
Office Action dated Nov. 20, 2006 for U.S. Appl. No. 09/709,162.
International Search Report PCT/US2004/23585.
Office Action dated Dec. 6, 2006 for U.S. Appl. No. 10/997,789.
Office Action dated Dec. 18, 2006 for U.S. Appl. No. 10/501,276.
Office Action dated Feb. 2, 2007 for U.S. Appl. No. 11/174,425.
International Search Report PCT/US2006/031905.
Office Action dated Mar. 28, 2007 for U.S. Appl. No. 11/241,907.
International Search Report PCT/US2007/060481.
Office Action dated May 23, 2007 for U.S. Appl. No. 10/406,751.
Office Action dated May 23, 2007 for U.S. Appl. No. 10/551,735.
International Search Report PCT/US2007/060717.
International Search Report PCT/US2007/060319.
Office Action dated Aug. 10, 2007 for U.S. Appl. No. 10/997,789.
International Search Report PCT/US2007/060657.
International Search Report PCT/US2007/061815.
International Search Report PCT/US2007/062465.
International Search Report PCT/US2007/066017.
European Patent Office Search Report for Application No. 01991092.6-2305.
International Search Report PCT/US2007/060670.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Office Action dated Oct. 30, 2007 for U.S. Appl. No. 11/670,069.
Office Action dated Nov. 15, 2007 for U.S. Appl. No. 11/285,301.
European Patent Office Search Report for Application No. 05791226.3.
Office Action dated Dec. 18, 2007 for U.S. Appl. No. 11/288,994.
Office Action dated Dec. 21, 2007 for U.S. Appl. No. 11/264,655.
Office Action dated Jan. 3, 2008 for U.S. Appl. No. 10/997,789.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
International Search Report PCT/US2007/061481 dated Mar. 17, 2008.
International Search Report PCT/US2007/078254 dated Mar. 28, 2008.
International Search Report for Application No. PCT/US2007/068233 dated Feb. 21, 2008.
International Search Report for Application No. PCT/US2007/060787 dated Mar. 18, 2008.
International Search Report and Written Opinion for Application No. PCT/US2007/061463 dated Jan. 23, 2008.
Fujimoto et al., "High Resolution in Vivo Intra-Arterial Imaging with Optical Coherence Tomography," *Official Journal of the British Cardiac Society*, vol. 82, pp. 128-133 Heart, 1999.
D. Huang et al., "Optical Coherence Tomography," *Science*, vol. 254, pp. 1178-1181, Nov. 1991.
Tearney et al., "High-Speed Phase—and Group Delay Scanning with a Grating Based Phase Control Delay Line," *Optics Letters*, vol. 22, pp. 1811-1813, Dec. 1997.
Rollins, et al., "In Vivo Video Rate Optical Coherence Tomography," *Optics Express*, vol. 3, pp. 219-229, Sep. 1998.
Saxer, et al., High Speed Fiber-Based Polarization-Sensitive Optical Coherence Tomography of in Vivo Human Skin, *Optical Society of America*, vol. 25, pp. 1355-1357.
Oscar Eduardo Martinez, "3000 Times Grating Compress or with Positive Group Velocity Dispersion," *IEEE*, vol. QE-23, pp. 59-64, Jan. 1987.
Kulkarni, et al., "Image Enhancement in Optical Coherence Tomography Using Deconvolution," *Electronics Letters*, vol. 33, pp. 1365-1367, Jul. 1997.
Bashkansky, et al., "Signal Processing for Improving Field Cross-Correlation Function in Optical Coherence Tomography," *Optics & Photonics News*, vol. 9, pp. 8137-8138, May 1998.
Yung et al., "Phase-Domain Processing of Optical Coherence Tomography Images," *Journal of Biomedical Optics*, vol. 4, pp. 125-136, Jan. 1999.
Tearney, et al., "In Vivo Endoscopic Optical Biopsy with Optical Coherence Tomography," *Science*, vol. 276, Jun. 1997.
W. Drexler et al., "In Vivo Ultrahigh-Resolution Optical Coherence Tomography," *Optics Letters* vol. 24, pp. 1221-1223, Sep. 1999.

(56) References Cited

OTHER PUBLICATIONS

Nicusor V. Iftimia et al., (2005) "A Portable, Low Coherence Interferometry Based Instrument for Fine Needle Aspiration Biopsy Guidance," Accepted to Review of Scientific Instruments, published May 23, 2005.
Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.
Agrawal, G.P., "Population Pulsations and Nondegenerate 4-Wave Mixing in Semiconductor-Lasers and Amplifiers," *Journal of the Optical Society of America B-Optical Physics*, vol. 5, pp. 147-159, Jan. 1998.
Andretzky, P. et al., "Optical Coherence Tomography by Spectral Radar: Improvement of Signal-to-Noise Ratio," *The International Society for Optical Engineering*, USA, vol. 3915, 2000.
Ballif, J. et al., "Rapid and Scalable Scans at 21 m/s in optical Low-Coherence Reflectometry," *Optics Letters*, vol. 22, pp. 757-759, Jun. 1997.
Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.
Beaud, P. et al., "Optical Reflectometry with Micrometer Resolution for the Investigation of Integrated Optical-Devices," *Leee Journal of Quantum Electronics*, vol. 25, pp. 755-759, Apr. 1989.
Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.
Brinkmeyer, E. et al., "Efficient Algorithm for Non-Equidistant Interpolation of Sampled Data," *Electronics Letters*, vol. 28, p. 693, Mar. 1992.
Brinkmeyer, E. et al., "High-Resolution OCDR in Dispersive Wave-Guides," *Electronics Letters*, vol. 26, pp. 413-414.
Chinn, S.R. et al., "Optical Coherence Tomography Using a Frequency-Tunable Optical Source," *Optics Letters*, vol. 22, pp. 340-342, Mar. 1997.
Danielson, B.L. et al., "Absolute Optical Ranging Using Low Coherence Interferometry," *Applied Optics*, vol. 30, p. 2975, Jul. 1991.
Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.
Eickhoff, W. et al., "Optical Frequency-Domain Reflectometry in Single-Mode Fiber," *Applied Physics Letters*, vol. 39, pp. 693-695, 1981.
Fercher, Adolf "Optical Coherence Tomography," *Journal of Biomedical Optics*, vol. 1, pp. 157-173, Apr. 1996.
Ferreira, L.A. et al., "Polarization-Insensitive Fiberoptic White-Light Interferometry," *Optics Communications*, vol. 114, pp. 386-392, Feb. 1995.
Fujii, Yohji, "High-Isolation Polarization-Independent Optical Circulator", *Journal of Lightwave Technology*, vol. 9, pp. 1239-1243, Oct. 1991
Glance, B., "Polarization Independent Coherent Optical Receiver," *Journal of Lightwave Technology*, vol. LT-5, p. 274, Feb. 1987.
Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.
Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.
Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.
Harvey, K. C. et al., "External-Cavity Diode-Laser Using a Grazing-Incidence Diffraction Grating," *Optics Letters*, vol. 16, pp. 910-912, Jun. 1991.
Hausler, Gerd et al., "'Coherence Radar' and 'Spectral Radar' New Tools for Dermatological Diagnosis," *Journal of Biomedical Optics*, vol. 3, pp. 21-31, Jan. 1998.
Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.
Hotate Kazuo et al., "Optical Coherence Domain Reflectometry by Synthesis of Coherence Function," *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.
Ivanov, A. P. et al., "New Method for High-Range Resolution Measurements of Light Scattering in Optically Dense Inhomogeneous Media," *Optics Letters*, vol. 1, pp. 226-228, Dec. 1977.
Ivanov, A. P. et al., "Interferometric Study of the Spatial Structure of a Light-Scattering Medium," *Journal of Applied Spectroscopy*, vol. 28, pp. 518-525, 1978.
Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.
Kersey, A. D. et al., "Adaptive Polarization Diversity Receiver Configuration for Coherent Optical Fiber Communications,"*Electronics Letters*, vol. 25, pp. 275-277, Feb. 1989.
Kolhaas, Andreas et al., "High Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.
Larkin, Kieran G., "Efficient Nonlinear Algorithm for Envelope Detection in White Light Interferometry." *Journal of the Optical Society of America A-Optics Image Science and Vision*, vol. 13, pp. 832-843, Apr. 1996.
Leitgeb, R. et al., "Spectral measurement of Absorption by Spectroscopic Frequency-Domain Optical Coherence Tomography," *Optics Letters*, vol. 25, pp. 820-822, Jun. 2000.
Lexer, F. et al., "Wavelength-Tuning Interferometry of Intraocular Distances," *Applied Optics*, vol. 36, pp. 6548-6553, Sep. 1997.
Mitsui, Takahisa, "Dynamic Range of Optical Reflectometry with Spectral Interometry," *Japanese Journal of Applied Physics Part 1—Regular Papers Short Notes & Review Papers*, vol. 38, pp. 6133-6137, 1999.
Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.
Okoshi,Takanori, "Polarization-State Control Schemes for Heterodyne or Homodyne Optical Fiber Communications," *Journal of Lightware Technology*, vol. LT-3, pp. 1232-1237, Dec. 1995.
Passy, R. et al., "Experimental and Theoretical Investigations of Coherent OFDR with Semiconductor-Laser Sources," *Journal of Lightwave Technology*, vol. 12, pp. 1622-1630, Sep. 1994.
Podoleanu, Adrian G., "Unbalanced Versus Balanced Operation in an Optical Coherence Tomography System," *Applied Optics*, vol. 39, pp. 173-182, Jan. 2000.
Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.
Schmitt, J. M. et al, "Measurement of Optical-Properties of Biological Tissues by Low-Coherence Reflectometry," *Applied Optics*, vol. 32, pp. 6032-6042, Oct. 1993.
Silberberg, Y. et al., "Passive-Mode Locking of a Semiconductor Diode-Laser," *Optics Letters*, vol. 9, pp. 507-509, Nov. 1984.

(56) References Cited

OTHER PUBLICATIONS

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.
Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.
Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.
Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.
Swanson, E. A. et al., "High-Speed Optical Coherence Domain Reflectometry," *Optics Letters*, vol. 17, pp. 151-153, Jan. 1992.
Takada, K. et al., "High-Resolution OFDR with Incorporated Fiberoptic Frequency Encoder," *IEEE Photonics Technology Letters*, vol. 4, pp. 1069-1072, Sep. 1992.
Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.
Takada, Kazumasa et al., "New Measurement System for Fault Location in Location in Optical Wave-Guide Devices Based on an Interometric-Technique," *Applied Optics*, vol. 26, pp. 1603-1606, May 1987.
Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.
Trutna, W. R. et al., "Continuously Tuned External-Cavity Semiconductor-Laser," *Journal of Lightwave Technology*, vol. 11, pp. 1279-1286, Aug. 1993.
Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.
Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.
Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.
Youngquist, Robert C. et al., "Optical Coherence-Domain Reflectometry—A New Optical Evaluation Technique," *Optics Letters*, vol. 12, pp. 158-160, Mar. 1987.
Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.
Yun, S. H. et al., "Interrogation of Fiber Grating Sensor Arrays with a Wavelength-Swept Fiber Laser," *Optics Letters*, vol. 23, pp. 843-845, Jun. 1998.
Yung, K. M., "Phase-Domain Processing of of Optical Coherence Tomography Images," *Journal Biomedical Optics*, vol. 4, pp. 125-136, Jan. 1999.
Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.
Zorabedian, Paul et al., "Tuning Fidelity of Acoustooptically Controlled External Cavity Semiconductor-Lasers," *Journal of Lightwave Technology*, vol. 13, pp. 62-66, Jan. 1995.
Victor S. Y. Lin et al., "A Porous Silicon-Based Optical Interferometric Biosensor," *Science Magazine*, vol. 278, pp. 840-843, Oct. 31, 1997.
De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.
Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.
Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.
Roth, Jonathan E. et al., "Simplified Method for Polarization-Sensitive Optical Coherence Tomography," *Optics Letters*, vol. 26, No. 14, Jul. 15, 2001, pp. 1069-1071.
Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.
Wang, Xuedong et al., (2001) "Propagation of Polarized Light in Birefringent Turbid Media: Time-Resolved Simulations," Optical Imaging Laboratory, Biomedical Engineering Program, Texas A&M University, Aug. 27, 2001, pp. 254-259.
Wong, Brian J.F. et al., "Optical Coherence Tomography of the Rat Cochlea," *Journal of Biomedical Optics*, vol. 5, No. 4, Oct. 2000, pp. 367-370.
Yao, Gang et al., "Propagation of Polarized Light in Turbid Media: Simulated Animation Sequences," *Optics Express*, vol. 7, No. 5, Aug. 28, 2000, pp. 198-203.
Wang, Xiao-Jun et al., "Characterization of Dentin and Enamel by Use of Optical Coherence Tomography," *Applied Optics*, vol. 38, No. 10, Apr. 1, 1999, pp. 2092-2096.
De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.
Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.
Groner, Warren et al., "Orthogonal Polarization Spectral Imaging: A New Method for the Study of the Microcirculation," *Nature Medicine Inc.*, vol. 5 No. 10, Oct. 1999, pp. 1209-1213.
De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.
Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.
Lu, Shih-Yau et al., "Homogeneous and Inhomogeneous Jones Matrices," *J. Opt. Soc. Am. A.*, vol. 11, No. 2, Feb. 1994, pp. 766-773.
Bickel, S. William et al., "Stokes Vectors, Mueller Matrices, and Polarized Scattered Light," *Am. J. Phys.*, vol. 53, No. 5, May 1985 pp. 468-478.
Bréhonnet, F. Le Roy et al., "Optical Media and Target Characterization by Mueller Matrix Decomposition," *J. Phys. D: Appl. Phys.* 29, 1996, pp. 34-38.
Cameron, Brent D. et al., "Measurement and Calculation of the Two-Dimensional Backscattering Mueller Matrix of a Turbid Medium," *Optics Letters*, vol. 23, No. 7, Apr. 1, 1998. pp. 485-487.
De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.
De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.
Everett, M.J. et al., "Birefringence Characterization of Biological Tissue by Use of Optical Coherence Tomography," *Optics Letters*, vol. 23, No. 3, Feb. 1, 1998, pp. 228-230.

(56) References Cited

OTHER PUBLICATIONS

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.
Barakat, Richard, "Statistics of the Stokes Parameters," *J. Opt. Soc. Am. B.*, vol. 4, No. 7, Jul. 1987, pp. 1256-1263.
Schmitt, J.M. et al., "Cross-Polarized Backscatter in Optical Coherence Tomography of Biological Tissue," *Optics Letters*, vol. 23, No. 13, Jul. 1, 1998, pp. 1060-1062.
Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.
Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1537-1536.
De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.
Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.
Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.
Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.
Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.
Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.
Ren, Hongwu et al., "Phase-Resolved Functional Optical Coherence Tomography: Simultaneous Imaging of In Situ Tissue Structure, Blood Flow Velocity, Standard Deviation, Birefringeence, and Stokes Vectors in Human Skin," *Optics Letters*, vol. 27, No. 19, Oct. 1, 2002, pp. 1702-1704.
Tripathi, Renu et al., "Spectral Shaping for Non-Gaussian Source Spectra in Optical Coherence Tomography," *Optics Letters*, vol. 27, No. 6, Mar. 15, 2002, pp. 406-408.
Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.
White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.
De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.
Jiao, Shuliang et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Mueller-Matrix Coherence Tomography and Application in Burn Imaging," *Applied Optics*, vol. 42, No. 25, Sep. 1, 2003, pp. 5191-5197.
Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stifter, D. et al., "Polarisation-Sensitive Optical Coherence Tomography for Material Characterisation and Strain-Field Mapping," *Applied Physics A 76*, Materials Science & Processing, Jan. 2003, pp. 947-951.
Davé, Digant P. et al., "Polarization-Maintaining Fiber-Based Optical Low-Coherence Reflectometer for Characterization and Ranging of Birefringence," *Optics Letters*, vol. 28, No. 19, Oct. 2003, pp. 1775-1777.
Yang, Ying et al., "Observations of Birefringence in Tissues from Optic-Fibre-Based Optical Coherence Tomography," *Measurement Science and Technology*, Nov. 2002, pp. 41-46.
Yun, S.H. et al., "High-Speed Optical Frequency-Domain Imaging," *Optics Express*, vol. 11, No. 22, Nov. 3, 2003, pp. 2953-2963.
Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Pircher, Michael et al., "Three Dimensional Polarization Sensitive OCT of Human Skin In Vivo," 2004, *Optical Society of America*.
Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.
Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.
Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.
Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.
Park, B. Hyle et al., Comment on "Optical-Fiber-Based Mueller Optical Coherence Tomography," *Optics Letters*, vol. 29, No. 24, Dec. 15, 2004, pp. 2873-2874.
Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

(56) References Cited

OTHER PUBLICATIONS

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorović, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimension heterodyne detection with a pain of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(60): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application For Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Birefringence Fibers" *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

(56) References Cited

OTHER PUBLICATIONS

Baumgartner, A., C. K. Hitzenberger, et al. (1998). "Signal and resolution enhancements in dual the human beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): with routine histology 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings os SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5):397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review* E 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

(56) References Cited

OTHER PUBLICATIONS

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.
Chen, Z. P., T. E. Milner, et al. (1997). "Optical Doppler tomographic imaging of fluid flow velocity in highly scattering media." *Optics Letters* 22(1): 64-66.
Chen, Z. P., T. E. Milner, et al. (1997). "Noninvasive imaging of in vivo blood flow velocity using optical Doppler tomography." *Optics Letters* 22(14): 1119-1121.
Chen, Z. P., Y. H. Zhao, et al. (1999). "Optical Doppler tomography." *Ieee Journal of Selected Topics in Quantum Electronics* 5(4): 1134-1142. .
Cheong, W. F., S. A. Prahl, et al. (1990). "A Review of the Optical-Properties of Biological Tissues." *Ieee Journal of Quantum Electronics* 26(12): 2166-2185.
Chernikov, S. V., Y. Zhu, et al. (1997). "Supercontinuum self-Q-switched ytterbium fiber laser." *Optics Letters* 22(5): 298-300.
Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.
Choma, M. A., M. V. Sarunic, et al. (2003). "Sensitivity advantage of swept source and Fourier domain optical coherence tomography." *Optics Express* 11(18): 2183-2189.
Choma, M. A., C. H. Yang, et al. (2003). "Instantaneous quadrature low-coherence interferometry with 3 x33 3 fiber-optic couplers." *Optics Letters* 28(22): 2162-2164.
Choplin, N. T. and D. C. Lundy (2001). "The sensitivity and specificity of scanning laser polarimetry in the detection of glaucoma in a clinical setting." *Ophthalmology* 108 (5): 899-904.
Christens Barry, W. A., W. J. Green, et al. (1996). "Spatial mapping of polarized light transmission in the central rabbit cornea." *Experimental Eye Research* 62(6): 651-662.
Chvapil, M., D. P. Speer, et al. (1984). "Identification of the depth of burn injury by collagen stainability." *Plastic & Reconstructive Surgery* 73(3): 438-41.
Cioffi, G. A. (2001). "Three common assumptions about ocular blood flow and glaucoma." *Survey of Ophthalmology* 45: S325-S331.
Coleman, A. L. (1999). "Glaucoma." *Lancet* 354(9192): 1803-10.
Collaborative Normal-Tension Glaucoma Study Group (1998). "Comparison of Glaucomatou Progression Between Untreated Patients With Normal Tension Glaucoma and Patients With Therapeutically Reduced Intraocular Pressures." *Am J Ophthalmol* 126: 487-97.
Collaborative Normal-Tension Glaucoma Study Group (1998). "The effectiveness of intraocular pressure reduction in the treatment of normal-tension glaucoma." *Am J Ophthalmol* 126: 498-505.
Collaborative Normal-Tension Glaucoma Study Group (2001). "Natural History of Normal-Tension Glaucoma." *Ophthalmology* 108: 247-253.
Colston, B. W., M. J. Everett, et al. (1998). "Imaging of hard- and soft-tissue structure in the oral cavity by optical coherence tomography." *Applied Optics* 37(16): 3582-3585.
Colston, B. W., U. S. Sathyam, et al. (1998). "Dental OCT" *Optics Express* 3(6): 230-238.
Congdon, N. G., D. S. Friedman, et al. (2003). "Important causes of visual impairment in the world today." *Jama-Journal of the American Medical Association* 290(15): 2057-2060.
Cregan, R. F., B. J. Mangan, et al. (1999). "Single-mode photonic band gap guidance of light in air." *Science* 285(5433): 1537-1539.
DalMolin, M., A. Galtarossa, et al. (1997). "Experimental investigation of linear polarization in high-birefringence single-mode fibers." *Applied Optics* 36(12): 2526-2528.
Danielson, B. L. and C. D. Whittenberg (1987). "Guided-Wave Reflectometry with Micrometer Resolution." *Applied Optics* 26(14): 2836-2842.
Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.
de Boer, J. F., C. E. Saxer, et al. (2001). "Stable carrier generation and phase-resolved digital data processing in optical coherence tomography." *Applied Optics* 40(31): 5787-5790.
Degroot, P. and L. Deck (1993). "3-Dimensional Imaging by Sub-Nyquist Sampling of White-Light Interferograms." *Optics Letters* 18(17): 1462-1464.
Denk, W., J. H. Strickler, et al. (1990). "2-Photon Laser Scanning Fluorescence Microscopy." *Science* 248(4951): 73-76.
Descour, M. R., A. H. O. Karkkainen, et al. (2002). "Toward the development of miniaturized Imaging systems for detection of pre-cancer." *Ieee Journal of Quantum Electronics* 38(2): 122-130.
Dettwiller, L. (1997). "Polarization state interference: A general investigation." *Pure and Applied Optics* 6(1): 41-53.
DiCarlo, C. D., W. P. Roach, et al. (1999). "Comparison of optical coherence tomography imaging of cataracts with histopathology." *Journal of Biomedical Optics* 4.
Ding, Z., Y. Zhao, et al. (2002). "Real-time phase-resolved optical coherence tomography and optical Doppler tomography." *Optics Express* 10(5): 236-245.
Dobrin, P. B. (1996). "Effect of histologic preparation on the cross-sectional area of arterial rings." *Journal of Surgical Research* 61(2): 413-5.
Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.
Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.
Drexler, W., A. Baumgartner, et al. (1997). "Biometric investigation of changes in the anterior eye segment during accommodation." *Vision Research* 37(19): 2789-2800.
Drexler, W., A. Baumgartner, et al. (1997). "Submicrometer precision biometry of the anterior segment of the human eye." *Investigative Ophthalmology & Visual Science* 38(7): 1304-1313.
Drexler, W., A. Baumgartner, et al. (1998). "Dual beam optical coherence tomography: signal identification for ophthalmologic diagnosis." *Journal of Biomedical Optics* 3 (1): 55-65.
Drexler, W., O. Findl, et al. (1998). "Partial coherence interferometry: A novel approach to biometry in cataract surgery." *American Journal of Ophthalmology* 126(4): 524-534.
Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.
Drexler, W., C. K. Hitzenberger, et al. (1998). "Investigation of dispersion effects in ocular media by multiple wavelength partial coherence interferometry." *Experimental Eye Research* 66(1): 25-33.
Drexler, W., C. K. Hitzenberger, et al. (1996) "(Sub)micrometer precision biometry of the human eye by optical coherence tomography and topography." *Investigative Ophthalmology & Visual Science* 37(3): 4374-4374.
Drexler, W., C. K. Hitzenberger, et al. (1995). "Measurement of the Thickness of Fundus Layers by Partial Coherence Tomography." *Optical Engineering* 34(3): 701-710.
Drexler, W., U. Morgner, et al. (2001). "Ultrahigh-resolution ophthalmic optical coherence tomography." *Nature Medicine* 7(4): 502-507.
Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

(56) References Cited

OTHER PUBLICATIONS

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique Reduction of Speckle for Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of theoral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation.* Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry*, Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*, Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

(56) References Cited

OTHER PUBLICATIONS

Gibson, G. N., R. Klank, et al. (1996). "Electro-optically cavity-dumped ultrashort-pulse Ti:sapphire oscillator." *Optics Letters* 21(14): 1055.
Gil, J. J. (2000). "Characteristic properties of Mueller matrices." *Journal of the Optical Society of America a-Optics Image Science and Vision* 17(2): 328-334.
Gil, J. J. and E. Bernabeu (1987). "Obtainment of the Polarizing and Retardation Paraments of a Nondepolarizing Optical-System from the Polar Decomposition of Its Mueller Matrix." *Optik* 76(2): 67-71.
Gladkova, N. D., G. A. Petrova, et al. (2000). "In vivo optical coherence tomography imaging of human skin: norm and pathology." *Skin Research and Technology* 6 (1): 6-16.
Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.
Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.
Goldberg, L. and D. Mehuys (1994). "High-Power Superluminescent Diode Source." *Electronics Letters* 30(20): 1682-1684.
Goldsmith, J. A., Y. Li, et al. (2005). "Anterior chamber width measurement by high speed optical coherence tomography." *Ophthalmology* 112(2): 238-244.
Goldstein, L. E., J. A. Muffat, et al. (2003). "Cytosolic beta-amyloid deposition supranuclear cataracts in lenses from people with Alzheimer's disease." *Lancet* 361(9365): 1258-1265.
Golubovic, B., B. E. Bouma, et al. (1996). "Thin crystal, room-temperature Cr/sup 4 +/:forstefite laser using near-infrared pumping." *Optics Letters* 21(24): 1993-1995.
Gonzalez, S. and Z. Tannous (2002). "Real-time, in vivo confocal reflectance microscopy of basal cell carcinoma." *Journal of the American Academy of Dermatology* 47(6): 869-874.
Gordon, M. O. and M. A. Kass (1999). "The Ocular Hypertension Treatment Study: design and baseline description of the participants." *Archives of Ophthalmology* 117(5): 573-83.
Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.
Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.
Greenfield, D. S., H. Bagga, et al. (2003). "Macular thickness changes in glaucomatous optic neuropathy detected using optical coherence tomography." *Archives of Ophthalmology* 121(1): 41-46.
Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.
Griffin, R. A., D. D. Sampson, et al. (1995). "Coherence Coding for Photonic Code-Division Multiple-Access Networks." *Journal of Lightwave Technology* 13(9): 1826-1837.
Guedes, V., J. S. Schuman, et al. (2003). "Optical coherence tomography measurement of macular and nerve fiber layer thickness in normal and glaucomatous human eyes." *Ophthalmology* 110(1): 177-189.
Gueugniaud, P. Y., H. Carsin, et al. (2000). "Current advances in the initial management of major thermal burns. [Review] [76 refs]." *Intensive Care Medicine* 26(7): 848-56.
Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.
Gurses-Ozden, R., H. Ishikawa, et al. (1999). "Increasing sampling density improves reproducibility of optical coherence tomography measurements." *Journal of Glaucoma* 8(4): 238-41.
Guzzi, R. (1998). "Scattering Theory from Homogeneous and Coated Spheres." 1-11.
Haberland, U. B., Vladimir; Schmitt, Hans J. (1996). "Optical coherent tomography of scattering media using electrically tunable near-infrared semiconductor laser." *Applied Optics* Draft Copy.
Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.
Hale, G. M. and M. R. Querry (1973). "Optical-Constants of Water in 200-Nm to 200-Mum Wavelength Region." *Applied Optics* 12(3): 555-563.
Hammer, D. X., R. D. Ferguson, et al. (2002) "Image stabilization for scanning laser ophthalmoscopy." *Optics Express* 10(26): 1542.
Hara, T., Y. Ooi, et al. (1989). "Transfer Characteristics of the Microchannel Spatial Light-Modulator." *Applied Optics* 28(22): 4781-4786.
Harland, C. C., S. G. Kale, et al. (2000). "Differentiation of common benign pigmented skin lesions from melanoma by high-resolution ultrasound." *British Journal of Dermatology* 143(2): 281-289.
Hartl, I., X. D. Li, et al. (2001). "Ultrahigh-resolution optical coherence tomography using continuum generation in an air-silica microstructure optical fiber." *Optics Letters* 26(9): 608-610.
Hassenstein, A., A. A. Bialasiewicz, et al. (2000). "Optical coherence tomography in uveitis patients." *American Journal of Ophthalmology* 130(5): 669-70.
Hattenhauer, M. G., D. H. Johnson, et al. (1998). "The probability of blindness from open-angle glaucoma. [see comments]." *Ophthalmology* 105(11): 2099-104.
Hausler, G., J. M. Herrmann, et al. (1996). "Observation of light propagation in volume scatterers with 10(11)-fold slow motion." *Optics Letters* 21(14): 1087-1089.
Hazebroek, H. F. and A. A. Holscher (1973). "Interferometric Ellipsometry." *Journal of Physics E-Scientific Instruments* 6(9): 822-826.
Hazebroek, H. F. and W. M. Visser (1983). "Automated Laser Interferometric Precision Reflectometry." *Journal of Physics E-Scientific Instruments* 16(7): 654-661.
He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.
Hee, M. R., J. A. Izatt, et al. (1993). "Femtosecond Transillumination Optical Coherence Tomography." *Optics Letters* 18(12): 950-952.
Hee, M. R., J. A. Izatt, et al. (1995). "Optical coherence tomography of the human retina." *Archives of Ophthalmology* 113(3): 325-32.
Hee, M. R., C. A. Puliafito, et al. (1998). "Topography of diabetic macular edema with optical coherence tomography." *Ophthalmology* 105(2): 360-70.
Hee, M. R., C. A. Puliafito, et al. (1995). "Quantitative assessment of macular edema with optical coherence tomography." *Archives of Ophthalmology* 113(8): 1019-29.
Hellmuth, T. and M. Welle (1998). "Simultaneous measurement of dispersion, spectrum, and distance with a fourier transform spectrometer." *Journal of Biomedical Optics* 3(1): 7-11.
Hemenger, R. P. (1989). "Birefringence of a medium of tenuous parallel cylinders." *Applied Optics* 28(18): 4030-4034.
Henry, M. (1981). "Fresnel-Arago Laws for Interference in Polarized-Light—Demonstration Experiment." *American Journal of Physics* 49(7): 690-691.
Herz, P. R., Y. Chen, et al. (2004). "Micromotor endoscope catheter for in vivo, ultrahigh-resolution optical coherence tomography." *Optics Letters* 29(19): 2261-2263.
Hirakawa, H., H. Iijima, et al. (1999). "Optical coherence tomography of cystoid macular edema associated with retinitis pigmentosa." *American Journal of Ophthalmology* 128(2): 185-91.
Hitzenberger, C. K., A. Baumgartner, et al. (1994). "Interferometric Measurement of Corneal Thickness with Micrometer Precision." *American Journal of Ophthalmology* 118(4): 468-476.

(56) References Cited

OTHER PUBLICATIONS

Hitzenberger, C. K., A. Baumgartner, et al. (1999). "Dispersion effects in partial coherence interferometry: Implications for intraocular ranging." *Journal of Biomedical Optics* 4(1): 144-151.
Hitzenberger, C. K., A. Baumgartner, et al. (1998). "Dispersion induced multiple signal peak splitting in partial coherence interferometry." *Optics Communications* 154(4): 179-185.
Hitzenberger, C. K., M. Danner, et al. (1999). "Measurement of the spatial coherence of superluminescent diodes." *Journal of Modern Optics* 46(12): 1763-1774.
Hitzenberger, C. K. and A. F. Fercher (1999). "Differential phase contrast in optical coherence tomography." *Optics Letters* 24(9): 622-624.
Hitzenberger, C. K., M. Sticker, et al. (2001). "Differential phase measurements in low-coherence interferometry without 2 pi ambiguity." *Optics Letters* 26(23): 1864-1866.
Hoeling, B. M., A. D. Fernandez, et al. (2000). "An optical coherence microscope for 3-dimensional imaging in developmental biology." *Optics Express* 6(7): 136-146.
Hoerauf, H., C. Scholz, et al. (2002). "Transscleral optical coherence tomography: a new imaging method for the anterior segment of the eye." *Archives of Ophthalmology* 120(6): 816-9.
Hoffmann, K., M. Happe, et al. (1998). "Optical coherence tomography (OCT) in dermatology." *Journal of Investigative Dermatology* 110(4): 583-583.
Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.
Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.
Holland, A. J. A., H. C. O. Martin, et al. (2002). "Laser Doppler imaging prediction of burn wound outcome in children." *Burns* 28(1): 11-17.
Hotate, K. and T. Okugawa (1994). "Optical Information-Processing by Synthesis of the Coherence Function." *Journal of Lightwave Technology* 12(7): 1247-1255.
Hourdakis, C. J. and A. Perris (1995). "A Monte-Carlo Estimation of Tissue Optical-Properties for Use in Laser Dosimetry." *Physics in Medicine and Biology* 40(3): 351-364.
Hu, Z., F. Li, et al. (2000). "Wavelength-tunable narrow-linewidth semiconductor fiber-ring laser." *IEEE Photonics Technology Letters* 12(8): 977-979.
Huang, F., W. Yang, et al. (2001). "Quadrature spectral interferometric detection and pulse shaping." *Optics Letters* 26(6): 382-384.
Huang, X. R. and R. W. Knighton (2002). "Linear birefringence of the retinal nerve fiber layer measured in vitro with a multispectral imaging micropolarimeter." *Journal of Biomedical Optics* 7(2): 199-204.
Huber, R., M. Wojtkowski, et al. (2005). "Amplified, frequency swept lasers for frequency domain reflectometry and OCT imaging: design and scaling principles." *Optics Express* 13(9): 3513-3528.
Hunter, D. G., J. C. Sandruck, et al. (1999). "Mathematical modeling of retinal birefringence scanning." *Journal of the Optical Society of America a-Optics Image Science and Vision* 16(9): 2103-2111.
Hurwitz, H. H. and R. C. Jones (1941). "A new calculus for the treatment of optical systems II. Proof of three general equivalence theorems." *Journal of the Optical Society of America* 31(7): 493-499.
Huttner, B., C. De Barros, et al. (1999). "Polarization-induced pulse spreading in birefringence optical fibers with zero differential group " *Optics Letters* 24(6): 370-372.
Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.
Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.
Hyde, S. C. W., N. P. Barry, et al. (1995). "Depth-Resolved Holographic Imaging through Scattering Media by Photorefraction." *Optics Letters* 20(11): 1331-1333.
Iftimia, N. V., B. E. Bouma, et al. (2004). "Adaptive ranging for optical coherence tomography." *Optics Express* 12(17): 4025-4034.
Iida, T., N. Hagimura, et al. (2000). "Evaluation of central serous chorioretinopathy with optical coherence tomography." *American Journal of Ophthalmology* 129(1): 16-20.
Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.
Indebetouw, G. and P. Klysubun (2000). "Imaging through scattering media with depth resolution by use of low-coherence gating in spatiotemporal digital holography." *Optics Letters* 25(4): 212-214.
Ip, M. S., B. J. Baker, et al. (2002). "Anatomical outcomes of surgery for idiopathic macular hole as determined by optical coherence tomography." *Archives of Ophthalmology* 120(1): 29-35.
Ismail, R., V. Tanner, et al. (2002). "Optical coherence tomography imaging of severe commotio retinae and associated macular hole." *British Journal of Ophthalmology* 86(4): 473-4.
Izatt, J. A., M. R. Hee, et al. (1994). "Optical Coherence Microscopy in Scattering Media." *Optics Letters* 19(8): 590-592.
Izatt, J. A., M. R. Hee, et al. (1994). "Micrometer-scale resolution imaging of the anterior eye in vivo with optical coherence tomography." *Archives of Ophthalmology* 112 (12): 1584-9.
Izatt, J. A., M. D. Kulkami, et al. (1997). "In vivo bidirectional color Doppler flow imaging of picoliter blood volumes using optical coherence tomography." *Optics Letters* 22(18): 1439-1441.
Izatt, J. A., M. D. Kulkami, et al. (1996). "Optical coherence tomography and microscopy in gastrointestinal tissues." *IEEE Journal of Selected Topics in Quantum Electronics* 2(4): 1017.
Jacques, S. L., J. S. Nelson, et al. (1993). "Pulsed Photothermal Radiometry of Port-Wine-Stain Lesions." *Applied Optics* 32(13): 2439-2446.
Jacques, S. L., J. R. Roman, et al. (2000). "Imaging superficial tissues with polarized light." *Lasers Lesions in Surgery and Medicine* 26(2): 119-129.
Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.
Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.
Jang, I. K., G. J. Tearney, et al. (2000). "Comparison of optical coherence tomography and intravascular ultrasound for detection of coronary plaques with large lipid-core in living patients." *Circulation* 102(18): 509-509.
Jeng, J. C., A. Bridgeman, et al. (2003). "Laser Doppler imaging determines need for excision and grafting in advance of clinical judgment: a prospective blinded trial." *Burns* 29(7): 665-670.
Jesser, C. A., S. A. Boppart, et al. (1999). "High resolution imaging of transitional cell carcinoma with optical coherence tomography: feasibility for the evaluation of bladder pathology," *British Journal of Radiology* 72: 1170-1176.
Johnson, C. A., J. L. Keltner, et al. (2002). "Baseline visual field characteristics in the ocular hypertension treatment study." *Ophthalmology* 109(3): 432-7.
Jones, R. C. (1941). "A new calculus for the treatment of optical systems III. The Sohncke theory of optical activity." *Journal of the Optical Society of America* 31 (7): 500-503.

(56) References Cited

OTHER PUBLICATIONS

Jones, R. C. (1941). "A new calculus for the treatment of optical systems I. Description and discussion of the calculus." *Journal of the Optical Society of America* 31(7): 488-493.
Jones, R. C. (1942). "A new calculus for the treatment of optical systems. IV." *Journal of the Optical Society of America* 32(8): 486-493.
Jones, R. C. (1947). "A New Calculus for the Treatment of Optical Systems .6. Experimental Determination of the Matrix." *Journal of the Optical Society of America* 37(2): 110-112.
Jones, R. C. (1947). "A New Calculus for the Treatment of Optical Systems .5. A More General Formulation, and Description of Another Calculus." *Journal of the Optical Society of America* 37(2): 107-110.
Jones, R. C. (1948). "A New Calculus for the Treatment of Optical Systems .7. Properties of the N-Matrices." *Journal of the Optical Society of America* 38(8): 671-685.
Jones, R. C. (1956). "New Calculus for the Treatment of Optical Systems .8. Electromagnetic Theory." *Journal of the Optical Society of America* 46(2): 126-131.
Jopson, R. MThe ., L. E. Nelson, et al. (1999). "Measurement of second-order polarization-mode dispersion vectors in optical fibers." *Ieee Photonics Technology Letters* 11 (9): 1153-1155.
Jost, B. M., A. V. Sergienko, et al. (1998). "Spatial correlations of spontaneously down-converted photon pairs detected with a single-photon-sensitive CCD camera." *Optics Express* 3(2): 81-88.
Kaplan, B., E. Compain, et al. (2000). "Phase-modulated Mueller ellipsometry characterization of scattering by latex sphere suspensions." *Applied Optics* 39 (4): 629-636.
Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.
Kasuga, Y., J. Arai, et al. (2000). "Optical coherence tomograghy to confirm early closure of macular holes." *American Journal of Ophthalmology* 130(5): 675-6.
Kaufman, T., S. N. Lusthaus, et al. (1990). "Deep Partial Skin Thickness Burns—a Reproducible Animal-Model to Study Burn Wound-Healing." *Burns* 16(1): 13-16.
Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.
Kerrigan-Baumrind, L. A., H. A. Quigley, et al. (2000) "Number of ganglion cells in glaucoma eyes compared with threshold visual field tests in the same persons." *Investigative Ophthalmology & Visual Science* 41(3): 741-8.
Kesen, M. R., G. L. Spaeth, et al. (2002). "The Heidelberg Retina Tomograph vs clinical impression in the diagnosis of glaucoma." *American Journal of Ophthalmology* 133(5): 613-6.
Kienle, A. and R. Hibst (1995). "A New Optimal Wavelength for Treatment of Port-Wine Stains." *Physics in Medicine and Biology* 40(10): 1559-1576.
Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.
Kim, B. Y. and S. S. Choi (1981). "Analysis and Measurement of Birefringence in Single-Mode Fibers Using the Backscattering Method." *Optics Letters* 6(11): 578-580.
Kimel, S., L. O. Svaasand, et al. (1994). "Differential Vascular-Response to Laser Photothermolysis." *Journal of Investigative Dermatology* 103(5): 693-700.
Kloppenberg, F. W. H., G. Beerthuizen, et al. (2001). "Perfusion of burn wounds assessed by Laser Doppler Imaging is related to burn depth and healing time." *Burns* 27(4): 359-363.
Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.
Knuettel, A. R. S., Joseph M.: Shay, M.; Knutson, Jay R. (1994). "Stationary low-coherence light imaging and spectroscopy using a CCD camera." *Proc. SPIE* , vol. 2135: p. 239-250.
Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.
Knuttel, A. and J. M. Schmitt (1993). "Stationary Depth-Profiling Reflectometer Based on Low-Coherence Interferometry." *Optics Communications* 102(3-4): 193-198.
Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.
Kobayashi, M., H. Hanafusa, et al. (1991). "Polarization-Independent Interferometric Optical-Time-Domain Reflectometer." *Journal of Lightwave Technology* 9(5): 623-628.
Kolios, M. C., M. D. Sherar, et al. (1995). "Large Blood-Vessel Cooling in Heated Tissues—a Numerical Study." *Physics in Medicine and Biology* 40(4): 477-494.
Koozekanani, D., K. Boyer, et al. (2001). "Retinal thickness measurements from optical coherence tomography using a Markov boundary model." *Ieee Transactions on Medical Imaging* 20(9): 900-916.
Kop, R. H. J. and R. Sprik (1995). "Phase-sensitive interferometry with ultrashort optical pulses." *Review of Scientific Instruments* 66(12): 5459-5463.
Kramer, R. Z., J. Bella, et al. (1999). "Sequence dependent conformational variations of collagen triple-helical structure." *Nature Structural Biology* 6(5): 454-7.
Kulkarni, M. D., T. G. van Leeuwen, et al. (1998). "Velocity-estimation accuracy and frame-rate limitations in color Doppler optical coherence tomography." *Optics Letters* 23(13): 1057-1059.
Kwon, Y. H., C. S. Kim, et al. (2001). "Rate of visual field loss and long-term visual outcome in primary open-angle glaucoma." *American Journal of Ophthalmology* 132(1): 47-56.
Kwong, K. F., D. Yankelevich, et al. (1993). "400-Hz Mechanical Scanning Optical Delay-Line." *Optics Letters* 18(7): 558-560.
Landers, J., I. Goldberg, et al. (2002). "Analysis of risk factors that may be associated with progression from ocular hypertension to primary open angle glaucoma." *Clin Experiment Ophthalmogy* 30(4): 242-7.
Laszlo, A. and A. Venetianer (1998). Heat resistance in mammalian cells: Lessons and challenges. *Stress of Life.* 851: 169-178.
Laszlo, A. and A. Venetianer (1998). "Heat resistance in mammalian cells: lessons and challenges [Review] [52 refs]." *Annals of the New York Academy of Sciences* 851: 169-78.
Laufer, J., R. Simpson, et al. (1998). "Effect of temperature on the optical properties of ex vivo human dermis and subdermis." *Physics in Medicine and Biology* 43(9): 2479-2489.
Lederer, D. E., J. S. Schuman, et al. (2003). "Analysis of macular volume in normal and glaucomatous eyes using optical coherence tomography." *American Journal of Ophthalmology* 135(6): 838-843.
Lee, P. P., Z. W. Feldman, et al. (2003). "Longitudinal prevalence of major eye diseases." *Archives of Ophthalmology* 121(9): 1303-1310.
Lehrer, M. S., T. T. Sun, et al. (1998). "Strategies of epithelial repair: modulation of stem cell and transit amplifying cell proliferation." *Journal of Cell Science* 111(Pt 19): 2867-75.
Leibowitz, H. M., D. E. Krueger, et al. (1980). "The Framingham Eye Study monograph: An ophthalmological and epidemiological study of cataract, glaucoma, diabetic retnopathy, macular degeneration, and visual acuity in a general population of 2631 adults, 1973-1975." *Survey of Ophthalmology* 24(Suppl): 335-610.
Leitgeb, R., C. K. Hitzenberger, et al. (2003). "Performance of fourier domain vs. time domain optical coherence tomography." *Optics Express* 11(8): 889-894.

(56) References Cited

OTHER PUBLICATIONS

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to acheive high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth-independent transversal resolution." *Journal of Modem Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefingence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Opthalmology* 106(10): 2027-32.

Mitsui, T. (1999). "High-speed detection of ballistic photons propagating through suspensions using spectral interferometry." *Japanese Journal of Applied Physics* Part 1—Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study, Study Design, MethodsR, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine in situ and in real time using optical Doppler tomography." *Archives of Dermatology* 137(6): 741-744.

(56) References Cited

OTHER PUBLICATIONS

Newson, T. P., F. Farahi, et al. (1988). "Combined Interferometric and Polarimetric Fiber Optic Temperature Sensor with a Short Coherence Length Source." *Optics Communications* 68(3): 161-165.
November, L. J. (1993). "Recovery of the Matrix Operators in the Similarity and Congruency Transformations—Applications in Polarimetry." *Journal of the Optical Society of America a-Optics Image Science and Vision* 10(4): 719-739.
Oh, W. Y., S. H. Yun, et al. (2005). "Wide tuning range wavelength-swept laser with two semiconductor optical amplifiers." *Ieee Photonics Technology Letters* 17(3): 678-680.
Oka, K. and T. Kato (1999). "Spectroscopic polarimetry with a channeled spectrum." *Optics Letters* 24(21): 1475-1477.
Okugawa, T. and K. Rotate (1996). "Real-time optical image processing by synthesis of the coherence function using real-time holography." *Ieee Photonics Technology Letters* 8(2): 257-259.
Oshima, M., R. Torii, et al. (2001). "Finite element simulation of blood flow in the cerebral artery." *Computer Methods in Applied Mechanics and Engineering* 191 (6-7): 661-671.
Pan, Y. T., H. K. Xie, et al. (2001). "Endoscopic optical coherence tomography based on a microelectromechanical mirror." *Optics Letters* 26(24): 1966-1968.
Parisi, V., G. Manni, et al. (2001). "Correlation between optical coherence tomography, pattern electroretinogram, and visual evoked potentials in open-angle glaucoma patients." *Ophthalmology* 108(5): 905-12.
Park, B. H., M. C. Pierce, et al. (2005). "Real-time fiber-based multi-functional spectral domain optical coherence tomography at 1.3 mu m." *Optics Express* 13(11): 3931-3944.
Park, D. H., J. W. Hwang, et al. (1998). "Use of laser Doppler flowmetry for estimation of the depth of burns." *Plastic and Reconstructive Surgery* 101(6): 1516-1523.
Pendry, J. B., A. J. Holden, et al. (1999). "Magnetism from conductors and enhanced nonlinear phenomena." *Ieee Transactions on Microwave Theory and Techniques* 47(11): 2075-2084.
Penninckx, D. and V. Morenas (1999). "Jones matrix of polarization mode dispersion." *Optics Letters* 24(13): 875-877.
Pierce, M. C., M. Shishkov, et al. (2005). "Effects of sample arm motion in endoscopic polarization-sensitive optical coherence tomography." *Optics Express* 13(15): 5739-5749.
Pircher, M., E. Gotzinger, et al. (2003). "Measurement and imaging of water concentration in human cornea with differential absorption optical coherence tomography." *Optics Express* 11(18):2190-2197.
Pircher, M., E. Gotzinger, et al. (2003). "Speckle reduction in optical coherence tomography by frequency compounding." *Journal of Biomedical Optics* 8(3): 565-569.
Podoleanu, A. G., G. M. Dobre, et al. (1998). "En-face coherence imaging using galvanometer scanner modulation." *Optics Letters* 23(3): 147-149.
Podoleanu, A. G. and D. A. Jackson (1999). "Noise analysis of a combined optical coherence tomograph and a confocal scanning ophthalmoscope." *Applied Optics* 38(10): 2116-2127.
Podoleanu, A. G., J. A. Rogers, et al. (2000). "Three dimensional OCT images from retina and skin." *Optics Express* 7(9): 292-298.
Podoleanu, A. G., M. Seeger, et al. (1998). "Transversal and longitudinal images from the retina of the living eye using low coherence reflectometry." *Journal of Biomedical Optics* 3(1): 12-20.
Poole, C. D. (1988). "Statistical Treatment of Polarization Dispersion in Single-Mode Fiber." *Optics Letters* 13(8): 687-689.
Povazay, B., K. Bizheva, et al. (2002). "Submicrometer axial resolution optical coherence tomography." *Optics Letters* 27(20): 1800-1802.
Qi, B., A. P. Himmer, et al. (2004). "Dynamic focus control in high-speed optical coherence tomography based on a microelectromechanical mirror." *Optics Communications* 232(1-6): 123-128.
Radhakrishnan, S., A. M. Rollins, et al. (2001). "Real-time optical coherence tomography of the anterior segment at 1310 nm." *Archives of Ophthalmology* 119(8): 1179-1185.
Rogers, A. J. (1981). "Polarization-Optical Time Domain Reflectometry—a Technique for the Measurement of Field Distributions." *Applied Optics* 20(6): 1060-1074.
Rollins, A. M. and J. A. Izatt (1999). "Optimal interferometer designs for optical coherence tomography." *Optics Letters* 24(21): 1484-1486.
Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.
Rollins, A. M., S. Yazdanfar, et al. (2002). "Real-time in vivo colors Doppler optical coherence tomography." *Journal of Biomedical Optics* 7(1): 123-129.
Rollins, A. M., S. Yazdanfar, et al. (2000). "Imaging of human retinal hemodynamics using color Doppler optical coherence tomography." *Investigative Ophthalmology & Visual Science* 41(4): S548-S548.
Sandoz, P. (1997). "Wavelet transform as a processing tool in white-light interferometry." *Optics Letters* 22(14): 1065-1067.
Sankaran, V., M. J. Everett, et al. (1999). "Comparison of polarized-light propagation in biological tissue and phantoms." *Optics Letters* 24(15): 1044-1046.
Sankaran, V., J. T. Walsh, et al. (2000). "Polarized light propagation through tissue phanto, ehms containing densely packed scatterers." *Optics Letters* 25(4): 239-241.
Sarunic, M. V., M. A. Choma, et al. (2005). "Instantaneous complex conjugate resolved spectral fiber domain and swept-source OCT using 3x33 3 couplers." *Optics Express* 13(3): 957-967.
Sathyam, U. S., B. W. Colston, et al. (1999). "Evaluation of optical coherence quantitation of analytes in turbid media by use of two wavelengths." *Applied Optics* 38(10): 2097-2104.
Schmitt, J. M. (1997). "Array detection for speckle reduction in optical coherence microscopy." *Physics in Medicine and Biology* 42(7): 1427-1439.
Schmitt, J. M. (1999). "Optical coherence tomography (OCT): A review." *Ieee Journal of Selected Topics in Quantum Electronics* 5(4): 1205-1215.
Schmitt, J. M. and A. Knuttel (1997). "Model of optical coherence tomography of heterogeneous tissue." *Journal of the Optical Society of America a-Optics Image Science and Vision* 14(6): 1231-1424.
Schmitt, J. M., S. L. Lee, et al. (1997). "An optical coherence microscope with enhanced resolving power in thick tissue." *Optics Communications* 142(4-6): 203-207.
Schmitt, J. M., S. H. Xiang, et al. (1998). "Differential absorption imaging with optical coherence tomography." *Journal of the Optical Society of America a-Optics Image Science and Vision* 15(9): 2288-2296.
Schmitt, J. M., S. H. Xiang, et al. (1999). "Speckle in optical coherence tomography." *Journal of Biomedical Optics* 4(1): 95-105.
Schmitt, J. M., M. J. Yadlowsky, et al. Coherence Microscopy. (1995). "Subsurface Imaging of Living Skin with Optical" *Dermatology* 191(2): 93-98.
Shi, H., J. Finlay, et al. (1997). "Multiwavelength 10-GHz picosecond pulse generation from a single-stripe semiconductor diode laser." *Ieee Photonics Technology Letters* 9(11): 1439-1441.
Shi, H., I. Nitta, et al. (1999). "Demonstration of phase correlation in multiwavelength mode-locked semiconductor diode lasers." *Optics Letters* 24(4): 238-240.
Simon, R. (1982). "The Connection between Mueller and Jones Matrices of Polarization Optics." *Optics Communications* 42(5): 293-297.
Smith, P. J. M., (2000) "Variable-Focus Microlenses as a Potential Technology for Endoscopy." SPIE (vol. 3919), USA pp. 187-192.
Smithies, D. J., T. Lindmo, et al. (1998). "Signal attenuation and localization in optical coherence tomography studied by Monte Carlo simulation." *Physics in Medicine and Biology* 43(10): 3025-3044.
Sorin, W. V. and D. F. Gray (1992). "Simultaneous Thickness and Group Index Measurement Using Optical Low-Coherence Reflectometry." *Ieee Photonics Technology Letters* 4(1): 105-107.

(56) References Cited

OTHER PUBLICATIONS

Sticker, M., C. K. Hitzenberger, et al. (2001). "Quantitative differential phase measurement and imaging in transparent and turbid media by optical coherence tomography." *Optics Letters* 26(8): 518-520.
Sticker, M., M. Pircher, et al. (2002). "En face imaging of single cell layers by differential phase-contrast optical coherence microscopy." *Optics Letters* 27(13): 1126-1128.
Stoller, P., B. M. Kim, et al. (2002). "Polarization-dependent optical second-harmonic imaging of a rat-tail tendon." *Journal of Biomedical Optics* 7(2): 205-214.
Sun, C. S. (2003). "Multiplexing of fiber-optic acoustic sensors in a Michelson interferometer configuration." *Optics Letters* 28(12): 1001-1003.
Swanson, E. A., J. A. Izatt, et al. (1993). "In-Vivo Retinal Imaging by Optical Coherence Tomography." *Optics Letters* 18(21): 1864-1866.
Takada, K., A. Himeno, et al. (1991). "Phase-Noise and Shot-Noise Limited Operations of Low Coherence Optical-Time Domain Reflectometry." *Applied Physics Letters* 59(20): 2483-2485.
Takenaka, H. (1973). "Unified Formalism for Polarization Optics by Using Group-Theory I (Theory)." *Japanese Journal of Applied Physics* 12(2): 226-231.
Tanno, N., T. Ichimura, et al. (1994). "Optical Multimode Frequency-Domain Reflectometer." *Optics Letters* 19(8): 587-589.
Tan-no, N., T. Ichimura, et al. (1994). "Optical Multimode Frequency-Domain Reflectometer." *Optics Letters* 19(8): 587-589.
Targowski, P., M. Wojtkowski, et al. (2004). "Complex spectral OCT in human eye imaging in vivo." *Optics Communications* 229(1-6): 79-84.
Tearney, G. J., S. A. Boppart, et al. (1996). "Scanning single-mode fiber optic catheter-endoscope for optical coherence tomography (vol. 21, p. 543, 1996)." *Optics Letters* 21(12): 912-912.
Teamey, G. J., B. E. Bouma, et al. (1996). "Rapid acquisition of in vivo biological images by use of optical coherence tomography." *Optics Letters* 21(17): 1408-1410.
Tearney, G. J., B. E. Bouma, et al. (1997). "In vivo endoscopic optical biopsy with optical coherence tomography." *Science* 276(5321): 2037-2039.
Tearney, G. J., M. E. Brezinski, et al. (1996). "Catheter-based optical imaging of a human coronary artery." *Circulation* 94(11): 3013-3013.
Tearney, G. J., M. E. Brezinski, et al. (1997). "In vivo endoscopic optical biopsy with optical coherence tomography." *Science* 276(5321): 2037-9.
Tearney, G. J., M. E. Brezinski, et al. (1997). "Optical biopsy in human gastrointestinal tissue using optical coherence tomography." *American Journal of Gastroenterology* 92(10): 1800-1804.
Tearney, G. J., M. E. Brezinski, et al. (1995). "Determination of the refractive index of highly scattering human tissue by optical coherence tomography." *Optics Letters* 20(21): 2258-2260.
Tearney, G. J., I. K. Jang, et al. (2000). "Porcine coronary imaging in vivo by optical coherence tomography." *Acta Cardiologica* 55(4): 233-237.
Tearney, G. J., R. H. Webb, et al. (1998). "Spectrally encoded confocal microscopy." *Optics Letters* 23(15): 1152-1154.
Tearney, G. J., H. Yabushita, et al. (2003). "Quantification of macrophage content in atherosclerotic plaques by optical coherence tomography." *Circulation* 107(1): 113-119.
Tower, T. T. and R. T. Tranquillo (2001). "Alignment maps of tissues: I. Microscopic elliptical polarimetry." *Biophysical Journal* 81(5): 2954-2963.
Tower, T. T. and R. T. Tranquillo (2001). "Alignment maps of tissues: II. Fast harmonic analysis for imaging." *Biophysical Journal* 81(5): 2964-2971.
Troy, T. L. and S. N. Thennadil (2001). "Optical properties of human skin in the near infrared wavelength range of 1000 to 2200 nm." *Journal of Biomedical Optics* 6 (2): 167-176.
Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.
Vakhtin, A. B., K. A. Peterson, et al. (2003). "Differential spectral interferometry: an imaging technique for biomedical applications." *Optics Letters* 28(15): 1332-1334.
Vakoc, B. J., S. H. Yun, et al. (2005). "Phase-resolved optical frequency domain imaging." *Optics Express* 13(14): 5483-5493.
van Leeuwen, T. G., M. D. Kulkarni, et al. (1999). "High-flow-velocity and shear-rate imaging by use of color Doppler optical coherence tomography." *Optics Letters* 24(22): 1584-1586.
Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.
Vargas, O., E. K. Chan, et al. (1999). "Use of an agent to reduce scattering in skin." *Lasers in Surgery and Medicine* 24(2): 133-141.
Wang, R. K. (1999). "Resolution improved optical coherence-gated tomography for imaging through biological tissues." *Journal of Modern Optics* 46(13): 1905-1912.
Wang, X. J., T. E. Milner, et al. (1997). "Measurement of fluid-flow-velocity profile in turbid media by the use of optical Doppler tomography." *Applied Optics* 36(1): 144-149.
Wang, X. J., T. E. Milner, et al. (1995). "Characterization of Fluid-Flow Velocity by Optical Doppler Tomography." *Optics Letters* 20(11): 1337-1339.
Wang, Y. M., J. S. Nelson, et al. (2003). "Optimal wavelength for ultrahigh-resolution optical coherence tomography." *Optics Express* 11(12): 1411-1417.
Wang, Y. M., Y. H. Zhao, et al. (2003). "Ultrahigh-resolution optical coherence tomography by a broadband continuum generation from photonic crystal fiber." *Optics Letters* 28(3): 182-184.
Watkins, L. R., S. M. Tan, et al. (1999). "Determination of interferometer phase distributions by use of wavelets." *Optics Letters* 24(13): 905-907.
Wetzel, J. (2001). "Optical coherence tomography in dermatology: a review." *Skin Research and Technology* 7(1): 1-9.
Wentworth, R. H. (1989). "Theoretical Noise Performance of Coherence-Multiplexed Interferometric Sensors." *Journal of Lightwave Technology* 7(6): 941-956.
Westphal, V., A. M. Rollins, et al. (2002). "Correction of geometric and refractive image distortions in optical coherence tomography applying Fermat's principle." *Optics Express* 10(9): 397-404.
Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515.
Wojtkowski, M., T. Bajraszewski, et al. (2003). "Real-time in vivo imaging by high-speed spectral optical coherence tomography." *Optics Letters* 28(19): 1745-1747.
Wojtkowski, M., A. Kowalczyk, et al. (2002). "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.
Yabushita, H. B., et al. (2002) "Measurement of Thin Fibrous Caps in Atherosclerotic Plaques by Optical Coherence Tomography." American Heart Association, INC, Circulation 2002;106;1640.
Yang, C., A. Wax, et al. (2001). "Phase-dispersion optical tomography." *Optics Letters* 26(10): 686-688.

(56) References Cited

OTHER PUBLICATIONS

Yang, C., A. Wax, et al. (2001). "Phase-referenced interferometer with subwavelength and subhertz sensitivity applied to the study of cell membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." Optics Communications 208(4-6): 209-214.
Yang, V. X. D., M. L. Gordon, et al. (2003). "High speed, wide velocity dynamic range Doppler optical coherence tomography (Part I): System design, signal processing, and performance." *Optics Express* 11(7): 794-809.
Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13): 424-431.
Yazdanfar, S., A. M. Rollins, et al. (2000). "Imaging and velocimetry of the human retinal circulation with color Doppler optical coherence tomography." *Optics Letters* 25(19): 1448-1450.
Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.
Yazdanfar, S., A. M. Rollins, et al. (2003). "In vivo imaging of human retinal flow dynamics by color Doppler optical coherence tomography." *Archives of Opthalmology* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength-swept laser for biomedical imaging." *Ieee Photonics Technology Letters* 16(1): 293-295.
Yun, S. H., C. Boudoux, et al. (2003). "High-speed wavelength-swept semiconductor laser with a polygon-scanner-based wavelength filter." *Optics Letters* 28(20): 1981-1983.
Yun, S. H., G. J. Tearney, et al. (2004). "Pulsed-source and swept-source spectral-domain optical coherence tomography with reduced motion artifacts." *Optics Express* 12(23): 5614-5624.
Yun, S. H., G. J. Tearney, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.
Zhang, Y., M. Sato, et al. (2001). "Numerical investigations of optimal synthesis of several low coherence sources for resolution improvement." *Optics Communications* 192(3-6): 183-192.
Zhang, Y., M. Sato, et al. (2001). "Resolution improvement in optical coherence tomography by optimal synthesis of light-emitting diodes." *Optics Letters* 26(4): 205-207.
Zhao, Y., Z. Chen, et al. (2002). "Real-time phase-resolved functional optical coherence tomography by use of optical Hilbert transformation." *Optics Letters* 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.
Zhou, D., P. R. Prucnal, et al. (1998). "A widely tunable narrow linewidth semiconductor fiber ring laser." *IEEE Photonics Technology Letters* 10(6): 781-783.
Zuluaga, A. F. and R. Richards-Kortum (1999). "Spatially resolved spectral interferometry for determination of subsurface structure." *Optics Letters* 24(8): 519-521.
Zvyagin, A. V., J. B. FitzGerald, et al. (2000). "Real-time detection technique for Doppler optical coherence tomography." *Optics Letters* 25(22): 1645-1647.
Marc Nikles et al., "Brillouin gain spectrum characterization in single-mode optical fibers", *Journal of Lightwave Technology* 1997, 15 (10): 1842-1851.
Tsuyoshi Sonehara et al., "Forced Brillouin Spectroscopy Using Frequency-Tunable Continuous-Wave Lasers", *Physical Review Letters* 1995, 75 (23): 4234-4237.
Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.
Webb RH et al. "Confocal Scanning Laser Ophthalmoscope", *Applied Optics* 1987, 26 (8): 1492-1499.
Andreas Zumbusch et al. "Three-dimensional vibrational imaging by coherent anti-Stokes Raman scattering", *Physical Review Letters* 1999, 82 (20): 4142-4145.
Katrin Kneipp et al., "Single molecule detection using surface-enhanced Raman scattering (SERS)", *Physical Review Letters* 1997, 78 (9): 1667-1670.
K.J. Koski et al., "Brillouin imaging" *Applied Physics Letters* 87, 2005.
Boas et al., "Diffusing temporal light correlation for burn diagnosis", *SPIE*, 1999, 2979:468-477.
David J. Briers, "Speckle fluctuations and biomedical optics: implications and applications", *Optical Engineering*, 1993, 32(2):277-283.
Clark et al., "Tracking Speckle Patterns with Optical Correlation", *SPIE*, 1992, 1772:77-87.
Facchini et al., "An endoscopic system for DSPI", *Optik*, 1993, 95(1):27-30.
Hrabovsky, M., "Theory of speckle dispacement and decorrelation: application in mechanics", *SPIE*, 1998, 3479:345-354.
Sean J. Kirkpatrick et al., "Micromechanical behavior of cortical bone as inferred from laser speckle data", *Journal of Biomedical Materials Research*, 1998, 39(3):373-379.
Sean J. Kirkpatrick et al., "Laser speckle microstrain measurements in vascular tissue", *SPIE*, 1999, 3598:121-129.
Loree et al., "Mechanical Properties of Model Atherosclerotic Lesion Lipid Pools", *Arteriosclerosis and Thrombosis*, 1994, 14(2):230-234.
Podbielska, H. "Interferometric Methods and Biomedical Research", *SPIE*, 1999, 2732:134-141.
Richards-Kortum et al., "Spectral diagnosis of atherosclerosis using an optical fiber laser catheter", *American Heart Journal*, 1989, 118(2):381-391.
Ruth, B. "blood flow determination by the laser speckle method", *Int J Microcirc: Clin Exp*, 1990, 9:21-45.
Shapo et al., "Intravascular strain imaging: Experiments on an Inhomogeneous Phantom", *IEEE Ultrasonics Symposium* 1996, 2:1177-1180.
Shapo et al., "Ultrasonic displacement and strain imaging of coronary arteries with a catheter array", *IEEE Ultrasonics Symposium* 1995, 2:1511-1514.

(56) References Cited

OTHER PUBLICATIONS

Thompson et al., "Imaging in scattering media by use of laser speckle", *Opt. Soc. Am. A.*, 1997, 14(9):2269-2277. .
Thompson et al., "Diffusive media characterization with laser speckle", *Applied Optics*, 1997, 36(16):3726-3734.
Tuchin, Valery V., "Coherent Optical Techniques for the Analysis of Tissue Structure and Dynamics," *Journal of Biomedical Optics*, 1999, 4(1):106-124.
M. Wussling et al., "Laser diffraction and speckling studies in skeletal and heart muscle", *Biomed, Biochim, Acta*, 1986, 45(1/2):S 23- 27.
T. Yoshimura et al., "Statistical properties of dynamic speckles", *J. Opt. Soc. Am A.* 1986, 3(7):1032-1054.
Zimnyakov et al., "Spatial speckle correlometry in applications to tissue structure monitoring", *Applied Optics* 1997, 36(22): 5594-5607.
Zimnyakov et al., "A study of statistical properties of partially developed speckle fields as applied to the diagnosis of structural changes in human skin", *Optics and Spectroscopy*, 1994, 76(5): 747-753.
Zimnyakov et al., "Speckle patterns polarization analysis as an approach to turbid tissue structure monitoring", SPIE 1999, 2981:172-180.
Ramasamy Manoharan et al., "Biochemical analysis and mapping of atherosclerotic human artery using FT-IR microspectroscopy", *Atherosclerosis*, May 1993, 181-1930.
N. V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", *Phys. Med. Biol.* 2000 (45): 1495-1509.
S.B. Adams Jr. et al., "The use of polarization sensitive optical coherence tomography and elastography to assess connective tissue", Optical Soc. of American Washington 2002, p. 3.
International Search Report for International Patent application No. PCT/US2005/039740 published Feb. 21, 2006.
International Written Opinion for International Patent application No. PCT/US2005/039740 published Feb. 21, 2006.
International Search Report for International Patent application No. PCT/US2005/030294 published Aug. 22, 2006.
International Written Opinion for International Patent application No. PCT/US2005/043951 published Apr. 6, 2006.
International Search Report for International Patent application No. PCT/US2005/043951 published Apr. 6, 2006.
Erdelyi et al. "Generation of diffraction-free beams for applications in optical microlithography", J. Vac. Sci. Technol. B 15 (12), Mar./Apr. 1997, pp. 287-292.
International Search Report for International Patent application No. PCT/US2005/023664 published Oct. 12, 2005.
International Written Opinion for International Patent application No. PCT/US2005/023664 published Oct. 12, 2005.
Tearney et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
International Search Report for International Patent application No. PCT/US2001/049704 published Dec. 10, 2002.
International Search Report for International Patent application No. PCT/US2004/039454 published May 11, 2005.
International Written Opinion for International Patent application No. PCT/US2004/039454 published May 11, 2005.
PCT International Preliminary Report on Patentability for International Application No. PCT/US2004/038404 dated Jun. 2, 2006.
Notice of Reasons for Rejection and English translation for Japanese Patent Application No. 2002-538830 dated May 12, 2008.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics Spie USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
PCT International Search Report and Written Opinion for Application No. PCT/US2004/023585 filed Jul. 23, 2004.
Elliott, K. H. "The use of commercial CCD cameras as linear detectors in the physics undergraduate teaching laboratory", European Journal of Physics, 1998, pp. 107-117.
Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.
Devesa, Susan S. et al. (1998) "Changing Patterns in the Incidence of Esophegeal Carcinoma and Gastric in the United States." *American Cancer Society* vol. 83, No. 10 pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" *Gastrorenterology* vol. 112, pp. 1787-1797.
Sepchler, Stuart Jon. (1997) "Barrett's Esophagus: Should We Brush off this Balloning Problem?" *Gastroenterology* vol. 112, pp. 2138-2152.
Froehly, J. et al. (2003) "Multiplexed 3D Imaging Using Wavelength Encoded Spectral Interferometry: A Proof of Principle" *Optics Communications* vol. 222, pp. 127-136.
Kubba A.K. et al. (1999) "Role of p53 Assessment in Management of Barrett's Esophagus" *Digestive Disease and Sciences* vol. 44, No. 4. pp. 659-667.
Reid, Brian J. (2001) "p53 and Neoplastic Progression in Barrett's Esophagus" *The American Journal of Gastroenterology* vol. 96, No. 5, pp. 1321-1323.

(56) References Cited

OTHER PUBLICATIONS

Sharma, P. et al.(2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209

Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.

Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.

Canto, Marcia Irene et al (1999) "Vital Staining and Barrett's Esophagus" *Gastrointestinal Endoscopy* vol. 49, No. 3, part 2, pp. 12-16.

Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.

Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* Col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis" Precise Microsurgery by Selective Absorption of Pulsed Radiation *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acoustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No. 7, pp. 1200-1209.

Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.

PCT International Search Report and Written Opinion for Application No. PCT/US2006/031905 dated May 3, 2007.

PCT International Search Report and Written Opinion for Application No. PCT/US2007/060481 dated May 23, 2007.

PCT International Search Report and Written Opinion for Application No. PCT/US2007/060717 dated May 24, 2007.

PCT International Search Report and Written Opinion for Application No. PCT/US2007/060319 dated Jun. 6, 2007.

D. Yelin et al., "Three-dimensional imaging using spectral encoding heterodyne interferometry", Optics Letters, Jul. 15, 2005, vol. 30, No. 14, pp. 1794-1796.

Akiba, Masahiro et al. "En-face optical coherence imaging for three-dimensional microscopy", SPIE, 2002, pp. 8-15.

(56) References Cited

OTHER PUBLICATIONS

PCT International Search Report and Written Opinion for Application No. PCT/US2007/060657 dated Aug. 13, 2007.
Lewis, Neil E. et al., (2006) "Applications of Fourier Transform Infrared Imaging Microscopy in Neurotoxicity", Annals New York Academy of Sciences, Dec. 17, 2006, vol. 820, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pythila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., (1999) "Speckle in Optical Coherence Tomography: An Overview", SPIE vol. 3726, pp. 450-461.
Siavash Yazdanfar et al., "In Vivo imaging in blood flow in human retinal vessels using color Doppler optical coherence tomography", SPIE, 1999 vol. 3598, pp. 177-184.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.

Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE—vol. 4001, 2000, pp. 92-101.
Lisauskas B. Jennifer et al., "Investigation of Plaque Biomechanics from Intravascular Ultrasound Images using Finite Element Modeling", Proceedings of the 19$^{th}$ International Conference—IEEE Oct. 30-Nov. 2, 1997, pp. 887-888.
Parker K. J. et al., "Techniques for Elastic Imaging: A Review", IEEE Engineering in Medicine and Biology, Nov./Dec. 1996, pp. 52-59.
European Patent Office Search Report dated Nov. 20, 2007 for European Application No. 05791226.3.
Dubois Arnaud et al., "Ultrahigh-resolution OCT using white-light interference microscopy", Proceedings of SPIE, 2003, vol. 4956, pp. 14-21.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
Notice of Reasons for Rejection dated Nov. 2, 2011 for JP 2008-509233.
Notice of Reasons for Rejection dated Nov. 21, 2011 for JP 2007-525075.
Extended European Search Report dated Nov. 28, 2011 for EP 09767845.2.
International Search Report and Written Opinion for PCT/US2011/037916 mailed Dec. 27, 2011.
International Search Report and Written Opinion for PCT/US2011/039066 mailed Dec. 28, 2011.
Communication pursuant to Article 94(3) for EP 10186189.6 mailed Dec. 22, 2011.
International Search Report and Written Opinion for PCT/US2011/038421 mailed Jan. 12, 2012.
Japanese Languange Appeal Decision mailed Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP2003516531.
International Search Report and Written Opinion mailed Feb. 9, 2012 based on PCT/US2011/034810.
European Search Report dated Mar. 2, 2012 for EP 11188120.7.

(56) References Cited

OTHER PUBLICATIONS

Japanese Notice of Reasons for Rejection dated Feb. 17, 2012 for JP 2007-539336.
Japanese Notice of Reasons for Rejection dated Feb. 15, 2012 for JP 2008-553509.
Japanese Notice of Reasons for Rejection dated Mar. 27, 2012 for JP 2008-554495.
Japanese Notice of Reasons for Rejection dated May 8, 2012 for JP 2008-533727.
Korean Office Action dated May 25, 2012 for KR 10-2007-7008116.
International Search Report and Written Opinion dated May 29, 2012 for PCT/US2011/058110.
International Search Report and Written Opinion dated May 29, 2012 for PCT/US2011/05007.
Japanese Notice of Reasons for Rejection dated Mar. 13, 2012 for JP2009-063553.
Japanese Notice of Reasons for Rejection dated May 21, 2012 for JP 2008-551523.
Japanese Notice Reasons for Rejection dated Jun. 20, 2012 for JP 2009-546534.
Japanese Notice of Reasons for Rejection dated Jun. 26, 2012 for JP 2002-585939.
European Official Action dated Aug. 1, 2012 for EP 10193526.0.
European Search Report dated Jun. 25, 2012 for EP 10733985.5.
European Communication Pursuant to EPC Article 94(3) for EP 07845206.7 dated Aug. 30, 2012.
International Search Report and Written Opinion mailed Aug. 30, 2012 for PCT/US2012/035234.
International Search Report and Written Opinion mailed on Aug. 16, 2012 for PCT/US2012/035887.
Japanese Notice of Reasons for Rejections dated Oct. 10, 2012 for 2008-553511.
Japanese Notice of Reasons for Rejections dated Oct. 2, 2012 for 2007-543626.
Canadian Office Action dated Oct. 10, 2012 for 2,514,189.
Japanese Notice of Reasons for Rejections dated Nov. 9, 2012 for 2007-530134.
Japanese Notice of Reasons for Rejection dated Nov. 27, 2012 for 2009-554772.
Japanese Notice of Reasons for Rejection dated Oct. 11, 2012 for 2008-533712.
Japanese Notice of Reasons for Rejection dated Dec. 18, 2012 for 2011-136398.
International Search Report and Written Opinion mailed Oct. 25, 2012 for PCT/US2012/047415.
Interntational Search Report and Written Opinion mailed on Aug. 16, 2012 for PCT/US2012/051132.
European Official Communications mailed on Feb. 11, 2013 for EP 08837490.5.
European Official Communication mailed on Feb. 15, 2012 for EP 04822169.1.
International Search Report mailed Jan. 31, 2013 for PCT/US2012/061135.
International Search Report and Written Opinion mailed Jan. 31, 2013 for PCT/US2012/060843.
European Search Report mailed on Mar. 11, 2013 for EP 10739129.4.
Notice of Reasons for Rejection dated Feb. 5, 2013 for JP 2008-509233.
Notice of Reasons for Rejection dated Feb. 19, 2013 for JP 2008-507983.
European Extended Search Report mailed Mar. 26, 2013 for EP 09825421.1.
International Search Report and Written Opinion mailed on Dec. 6, 2012 for PCT/US2012/052553.
European Extended Search Report mailed on Feb. 1, 2013 for EP 12171521.3.
Official European Search report mailed on Apr. 24, 2013 for EP 10182341.7.

Notice of Reasons for Rejection mailed on Apr. 16, 2013 for JP 2008-533727.
Notice of Reasons for Rejection mailed on Apr. 16, 2013 for JP 2009-510092.
Notice of Reasons for Rejection mailed on May 7, 2013 for JP 2011-508674.
European Search Report for 12194876.4 dated Feb. 1, 2013.
Japanese Notice of Reasons for Rejection for 2010-529142 dated Jan. 29, 2013.
Japanese Notice of Reasons for Rejection for 2007-539336 dated May 21, 2013.
International Search Report and Written Opinion for PCT/US2013/022136.
European Official Communications dated Jun. 28, 2013 for EP 09158713.9.
Japanese Notice of Reasons for Rejection for 2013-026897 dated Jun. 6, 2013.
Japanese Notice of Reasons for Rejection for 2013-026880 dated Jun. 6, 2013.
International Application Search Report and Written Opinion dated Apr. 11, 2013 for PCT/US2013/021299.
Extended European Search Report dated Jul. 2, 2013 for EP 10738929.8.
European Search Report dated Jul. 15, 2013 for EP 10800455.7.
European Search Report dated Jul. 26, 2013 for EP 09743687.7.
Extended European Search Report dated Jul. 11, 2013 for EP 09832543.4.
Japanese Office Action dated Aug. 20, 2013 for JP 2011-546443.
International Search Report and Written Opinion dated Sep. 19, 2013 for PCT/US2013/042008.
Japanese Notice of Reasons for Rejection dated Jul. 16, 2013 for JP 2009-063553.
Korean Notification of Ground for Rejection dated Sep. 30, 2013 for 10-2007-7027721.
European Search Report dated Sep. 10, 2013 for EP 10183412.5.
Japanese Official Action dated Oct. 15, 2013 for JP 2012-181098.
Japanese Office Action dated Oct. 8, 2013 for JP 2011-168738.
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: Double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Reasons for Rejection dated Dec. 12, 2011 for JP 2008-533712.
Japanese Notice of Reasons for Rejection dated Mar. 27, 2012 for JP 2003-102672.
Japanese Notice of Reasons for Rejection dated Jun. 20, 2012 for JP 2009-546534.
European Official Communication dated Aug. 1, 2012 for EP 10193326.0.
European Search Report dated Jun. 23, 2012 for EP 10733985.5.
Wieser, Wolfgang et al., "Multi-Megahertz OCT: Hight Quality 3D Imaging at 20 million A-Scans and 4.5 Gvoxels Per Second" Jul. 5, 2010, vol. 18, No. 14, Optics Express.
Giuliano Scarcelli et al., "Three-Dimensional Brillouin Confocal Microscopy". Optical Society of American, 2007, CtuV5.
Giuliano, Scarcelli et al., "Confocal Brilloun Microscopy for Three-Dimensional Mechanical Imaging." Nat Photonis, Dec. 9, 2007.
Japanese Notice of Reasons for Rejections dated Oct. 10, 2012 for 2008-553511 1O.
W.Y. Oh et al: "High-Speed Polarization Sensitive Optical Frequency Domain Imaging with Frequency Multiplexing", Optics Express, vol. 16, No. 2, Jan. 1, 2008.
Athey, B.D. et al., "Development and Demonstration of a Networked Telepathology 3-D Imaging, Databasing, and Communications System", 1998 ("C2"), pp. 5-17.

(56) References Cited

OTHER PUBLICATIONS

D'Amico, A.V., et al., "Optical Coherence Tomography as a Method for Identifying Benign and Maliganat Microscopic Structures in the Prostate Gland", Urology, vol. 55, Isue 5, May 2000 ("C3"), pp. 783-787.

Tearney, G.J. et al., "In Vivo Endoscopic Optical Biopsy with Optical Coherence Tomography", Science, vol. 276, No. 5321, Jun. 27, 1997 ("C6"), pp. 2037-2039.

Japanese Notice of Reasons for Rejections dated Nov. 9, 2012 for JP 2007-530134.

Japanese Notice of Reasons for Rejections dated Nov. 27, 2012 for JP 2009-554772.

Japanese Notice of Reasons for Rejections dated Oct. 11, 2012 for JP 2008-533712.

Yoden, K. et al. "An Approach to Optical Reflection Tomography Along the Geometrial Thickness," Optical Review, vol. 7, No. 5, Oct. 1, 2000.

Joshua, Fox et al: "Measuring Primate RNFL Thickness with OCT", IEEE Journal of Selected Topics in Quantum Electronics, IEEE Service Center, Piscataway, NJ, US, vol. 7,No. 6, Nov. 1, 2001.

European Official Communication dated Feb. 6, 2013 for 0482 2169.1.

Viliyam K. Pratt. Lazernye Sistemy Svyazi. Moskva, Izdatelstvo "Svyaz", 1972. p. 68-70.

European Search Report mailed on Mar. 11, 2013 doe EP 1073 9129.4.

Huber, R et al: "Fourier Domain Mode Locked Lasers for OCT Imaging at up to 290 kHz Sweep Rates", Proceedings of SPIE, SPIE—International Society for Optical Engineering, US, vol. 5861, No. 1, Jan. 1, 2005.

M. Kourogi et al: "Programmable High Speed (1MHz) Vernier-mode-locked Frequency-Swept Laser for OCT Imaging", Proceedings of SPIE, vol. 6847, Feb. 7, 2008.

Masahiro, Yamanari et al: "polarization-Sensitive Swept-Source Optical Coherence Tomography with Continuous Source Polarization Modulation", Optics Express, vol. 16, No. 8, Apr. 14, 2008.

Nakamura, Koichiro et al., "A New Technique of Optical Ranging by a Frequency-Shifted Feedback Laser", IEEE Phontonics Technology Letters, vol. 10, No. 12, pp. 1041-1135, Dec. 1998.

Lee, Seok-Jeong et al., "Ultrahigh Scanning Speed Optical Coherence Tomography Using Optical Frequency Comb Generators", The Japan Soceity of Applied Physics, vol. 40 (2001).

Kinoshita, Masaya et al., "Optical Frequency-Domain Imaging Microprofilmetry with a Frequency-Tunable Liquid-Crystal Fbry-Perot Etalon Device" Applied Optics, vol. 38, No. 34, Dec. 1, 1999.

Bachmann A.H. et al: "Heterodyne Fourier Domain Optical Coherence Tomography for Full Range Probing with High Axial Resolution", Optics Express, OSA, vol. 14, No. 4, Feb. 20, 2006.

Thomas J. Flotte: "Pathology Correlations with Optical Biopsy Techniques", Annals of the New York Academy of Sciences, Wiley-Blackwell Publishing, INC. SU, vol. 838, No. 1, Feb. 1, 1998, pp. 143-149.

Constance R. Chu et al: Arthroscopic Microscopy of Articular Cartilage Using Optical Coherence Tomography, American Journal of Sports Medicine, American Orthopedic Society for Sports Medicine, Waltham, MA, Vo. 32, No. 9, Apr. 1, 2004.

Bouma B E et al: Diagnosis of Specialized Intestinal Metaplasia of the Esophagus with Optical Coherence Tomography, Conference on Lasers and Electro-Optics. Technical Digest. OSA, US, vol. 56, May 6, 2001.

Shen et al: "Ex Vivo Histology-Correlated Optical Coherence Tomography in the Detection of Transmural Inflammation in Crohn's Disease", Clinical Gastroenterology and Heptalogy, vol. 2, No. 9, Sep. 1, 2004.

Shen et al: "In Vivo Colonscopic Optical Coherence Tomography for Transmural Inflammation in Inflammatory Bowel Disease", Clinical Gastroenterology and Hepatology, American Gastroenterological Association, US, vol. 2, No. 12, Dec. 1, 2004.

Ge Z et al: "Identification of Colonic Dysplasia and Neoplasia by Diffuse Reflectance Spectroscopy and Pattern Recognition Techniques", Applied Spectroscopy, The Society for Applied Spectroscopy, vol. 52, No. 6, Jun. 1, 1998.

Elena Zagaynova et al: "Optical Coherence Tomography: Potentialities in Clinical Practice", Proceedings of SPIE, Aug. 20, 2004.

Westphal et al: "Correlation of Endoscopic Optical Coherence Tomography with Histology in the Lower-GI Tract", Gastrointestinal Endoscopy, Elsevier, NL, vol. 61, No. 4, Apr. 1, 2005.

Haggitt et al: "Barrett's Esophaagus, Dysplasia, and Adenocarcinoma", Human Pathology, Saunders, Philadelphia, PA, US, vol. 25, No. 10, Oct. 1, 1994.

Gang Yao et al. "Monte Carlo Simulation of an Optical Coherence Tomography Signal in Homogenous Turbid Media," Physics in Medicine and Biology, 1999.

Murakami, K. "A Miniature Confocal Optical Scanning Microscopy for Endscopes", Proceedings of SPIE, vol. 5721, Feb. 28, 2005, pp. 119-131.

Seok, H. Yun et al: "Comprehensive Volumetric Optical Microscopy in Vivo", Nature Medicine, vol. 12, No. 12, Jan. 1, 2007.

Baxter: "Image Zooming", Jan. 25, 2005, Retrieved from the Internet.

Qiang Zhou et al: "A Novel Machine Vision Application for Analysis and Visualization of Confocal Microscopic Images" Machine Vision and Applications, vol. 16, No. 2, Feb. 1, 2005.

Igor Gurov et al: (2007) "Full-field High-Speed Optical Coherence Tomography System for Evaluting Multilayer and Random Tissues", Proc. of SPIE, vol. 6618.

Igor Gurov et al: "High-Speed Signal Evaluation in Optical Coherence Tomography Based on Sub-Nyquist Sampling and Kalman Filtering Method" AIP Coherence Proceedings, vol. 860, Jan. 1, 2006.

Groot De P et al: "Three Dimensional Imaging by Sub-Nyquist Sampling of White-Light Interferograms", Optics Letters, vol. 18, No. 17, Sep. 1, 1993.

Silva et al: "Extended Range, Rapid Scanning Optical Delay Line for Biomedical Interferometric Imaging", Electronics Letters, IEE Stevenage, GB vol. 35, No. 17, Aug. 19, 1999.

\* cited by examiner

IMAGING SYSTEM, METHOD AND DISTAL ATTACHMENT FOR MULTIDIRECTIONAL FIELD OF VIEW ENDOSCOPY

CROSS-REFERENCE TO RELATED APPLICATIONS

This application based upon and claims the benefit of priority from International Application No. PCT/US2013/031948 filed on Mar. 15, 2013, which claims the benefit of priority from U.S. Provisional Patent Application Ser. No. 61/618,225, filed Mar. 30, 2012, the entire disclosures of which are incorporated herein by reference.

FIELD OF THE DISCLOSURE

Exemplary embodiments of the present disclosure relate to endoscopic imaging system and methods for multidirectional field of view endoscopy which can be used to improve the field of view, speed and efficiency of diagnostic and therapeutic endoscopic procedures.

BACKGROUND OF THE DISCLOSURE

In general, endoscopic imaging systems allow the evaluation of animal and human internal organs. Endoscopes can consist of at least one of the following components, a rigid or flexible tube, a light delivery system, a fluid delivery and recovery system, an air delivery and recovery system, a lens system, an eyepiece, a high pixel-count color CCD or imaging transmission system, graphical display unit (monitor), and/or accessory channel(s) to allow use of devices for manipulation, sampling or imaging of target lesions.

The endoscope may be inserted into any natural orifice of the animal or human including the nares, ears, mouth, biliary tract, pancreatic duct, ostomy, urinary tract, vagina, uterus, fallopian tubes, anus and/or any opening produced by procedures employing an incision or puncture into an internal body cavity (craniotomy, thoracotomy, mediastinotomy, laparotomy or arthrotomy). While currently available endoscopes are capable of evaluating target structures by the obligatory forward or other directional field of view obtained by current light delivery and lens systems, in some medical applications this design increases the risk for missed detection of important areas of interest. As a result, there is a need for multi-directional visualization.

Colonoscopy is widely considered the gold standard for detecting mucosal abnormalities in the human colon, and the preferred technique for removal of many non-invasive lesions requires biopsy, polypectomy or endoscopic resection. There have been well-documented limitations related to the practice of colonoscopy with traditional endoscopic instruments. Because most colon cancers are believed to arise from abnormal colon tissue, adenomas, the detection and removal of adenomatous polyps have been recommended for the prevention of future colon cancers. (See, e.g., ref. 1). Missed polyps or cancers have been one of these unfortunate limitations. (See, e.g., refs. 2-4). Although there are additional factors associated with the risks of missing mucosal lesions such as, a patient's colonic anatomy, patient comfort during an endoscopic procedure and the quality of bowel preparation, it has been well established by other investigators, that the location of mucosal abnormalities is highly associated with failure of identification. (See, e.g., ref. 4).

Prior groups have investigated several approaches to attempt to demonstrate an improvement in the diagnostic yield of a colonoscopic procedure by altering or increasing the conventional forward fields of view. Unfortunately these studies did not demonstrate a significant increase in adenoma detection. (See, e.g., refs. 5-7). Nevertheless, the uses of a transparent cap that does not change or improve the field of view placed on the distal aspect of colonoscopes have demonstrated great promise in improving the effectiveness of colonoscopy (see, e.g., refs. 8-11) and adenoma detection (see, e.g., ref. 12), however the use of these devices are still associated with a significant adenoma miss rate. (See, e.g., ref. 13).

Other researchers have attempted to improve the adenoma detection rate established with the use of a conventional endoscopic system by increasing the total field of view during a colonoscopy by coupling the traditional endoscope with an auxiliary imaging device, placed within the accessory channel, to provide a continuous retrograde view of the target organ via the accessory channel. (See, e.g., ref. 14). While this auxiliary imaging device provides a continuous retrograde field of view used in combination with traditional forward viewing endoscopes, it requires the use of an accessory channel of the endoscope. This becomes an important factor during colonoscopy, if used with a standard single channel colonoscope, due to the necessity to remove the auxiliary imaging device to allow for the use of an appropriate auxiliary sampling or retrieval instrument to biopsy, resect and retrieve specimens removed from the organ being investigated. This additional equipment has been shown in a prospective, multicenter, randomized, controlled trial to decrease the relative risk of missing polyps and adenomas but was also shown to have a statistically significant increase in the mean total procedure times.[15] Auxiliary endoscopic devices placed within the auxiliary channel of the endoscope have the further disadvantage that they require an additional endoscope, which increases complexity, ease of use, and cost of the overall procedure.

Thus, there is a need to address at least some of the issues and/or deficiencies described herein above.

SUMMARY OF EXEMPLARY EMBODIMENTS

In various exemplary embodiments according to the present disclosure, exemplary configurations for the acquisition of multidirectional viewing during endoscopic examination can be provided. Exemplary applications can be utilized, in which increasing the field of view while using high resolution endoscopic systems can be improved with the exemplary embodiments of the system and method of continuous and simultaneous forward and multidirectional views during a baroscopic, laparoscopic, angioscopic, or endoscopic procedure.

Exemplary embodiments of the present disclosure can relate generally to exemplary configuration of optical elements, and to the application(s) thereof in exemplary endoscopic imaging systems which can be used with medical applications to improve the field of view, speed and efficiency of an endoscopic procedure. Exemplary embodiments of the present disclosure can be applied to rigid, flexible, wireless or telescoping endoscope to provide, e.g., a continuous multi-directional view of animate and inanimate hollow spaces.

In one further exemplary embodiment of the present disclosure, a distal imaging attachment and an imaging system can be used in combination with a rigid, flexible, wireless or telescoping endoscope to create a continuous multi-directional view of animate and inanimate hollow spaces. According to a further exemplary embodiment of the present disclosure, the directions are forward and to the side. In yet another preferred embodiment of the present disclosure, the directions are forward and backward. In still yet another further embodiment, the directions cover approximately a 4pi solid angle that is only obscured by the device itself. This said distal imaging attachment and imaging system may be employed, but not limited to, with endoscopy of animal and human internal anatomical organs and borescopy of inanimate closed spaces. Due to its design, the integrated optical element within this imaging system, allowing both the forward and multidirectional fields of view.

In yet further exemplary embodiment of the present disclosure, it is also possible to accommodate the simultaneous passage of devices via the accessory channel of a video endoscope or applicable device of which the distal imaging attachment is applied. For example, optical elements in the exemplary device can be configured to facilitate a multidirectional viewing of target organs or spaces with exemplary endoscopes. In another exemplary embodiment of the present disclosure, the exemplary device can be retrofitted to alter the native conventional high definition endoscopes currently used in endoscopic procedures. In still further exemplary embodiment of the present disclosure, the exemplary device/apparatus can be disposable.

Indeed, exemplary embodiments according to the present disclosure as described herein, can be provided as exemplary endoscopic lens system(s), and can be termed as "multidirectional", "simulview" or "retroview", and utilized as a basis for exemplary embodiments of endoscopic systems for a deployment.

Further, an exemplary apparatus for imaging at least one anatomical structure can be provided, according to an exemplary embodiment of the present disclosure. For example, the apparatus can include an endoscopic first arrangement, a radiation source second arrangement which provides at least one electro-magnetic radiation, and a third arrangement attached to at least one portion of the endoscopic arrangement. The third arrangement can contain an optical arrangement which, upon impact by the at least one electromagnetic radiation and based thereon, may transmit a first radiation and reflects a second radiation. The first radiation can impact at least one first portion of the anatomical structure(s), and the second radiation can impact at least one second portion of the anatomical structure(s). The first and second portions can be at least partially different from one another. Further, the first and second radiations can have characteristics which are different from one another.

For example, the characteristics can include or be wavelengths or polarizations. A detector arrangement can be provided, whereas the endoscopic arrangement can be associated with the radiation source arrangement and the detector arrangement. The first and second radiations can have spectral regions in red, green and blue band which do not substantially overlap with one another. The first radiation can be directed in a forward direction, and the second radiation can be directed in a backward direction or a side direction. The third arrangement can include a cap that can be connected to an end portion of the endoscopic first arrangement. The second radiation can simultaneously illuminate between 270 and 360 degrees of a field of view. Further, the radiation source second arrangement can include a modulation arrangement which can be configured to modulate the first and second radiations. An electronic arrangement can be provided which is configured to synchronize the second arrangement and the detector arrangement. As an alternative or in addition, the electronic arrangement can be configured to (i) synchronize the modulation arrangement and the detector arrangement, and (ii) control the detector arrangement to detect signals from the anatomical structure(s) illuminated by the first and second radiation, and separate the signals based the synchronization with the modulation arrangement.

According to further exemplary embodiments of the present disclosure, the anatomical structure(s) can be a luminal anatomical structure. The third arrangement can include at least one opening which facilitates a passage of instrumentation, air gasses and/or fluids therethrough. A tube can be provided that is associated with the third arrangement, and which provide a passage of instrumentation, air gasses and/or fluids therethrough. Further, the first and second radiations can have a specific polarization status.

Other features and advantages of the present invention will become apparent upon reading the following detailed description of exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
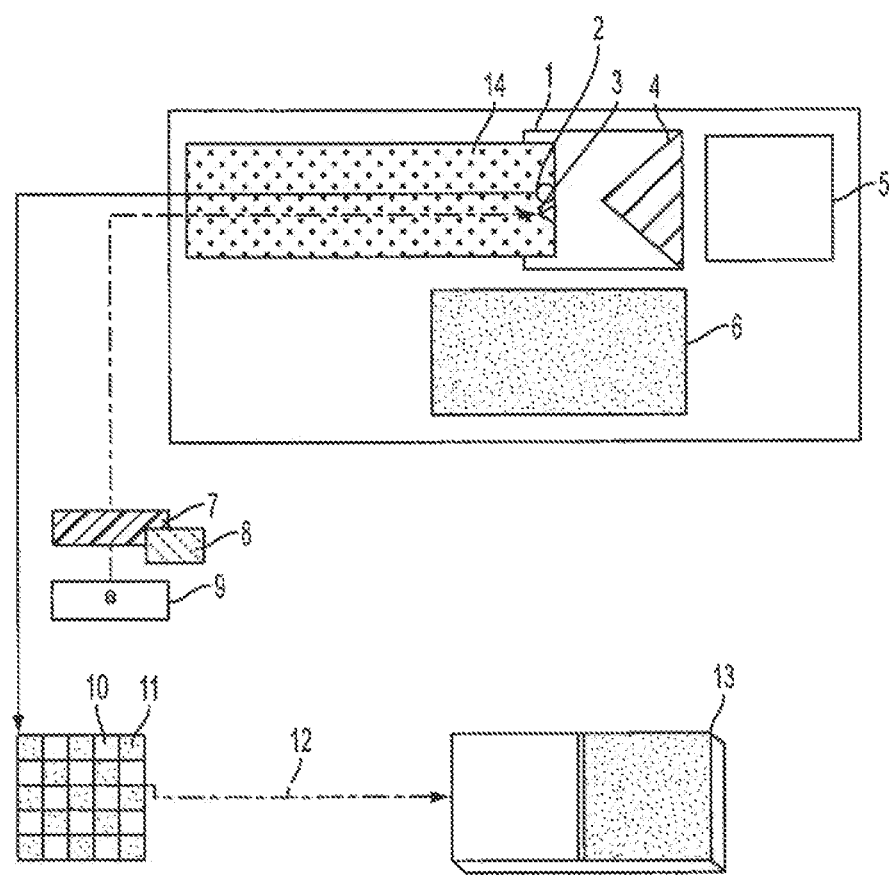
FIG. 1 is a side cross-sectional block diagram of an imaging system/apparatus and optical elements thereof according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures, and/or the appended claims.

DETAILED DESCRIPTION OF EXEMPLARY EMBODIMENTS

Using the exemplary embodiments of the apparatus, system and method of the present disclosure, it is possible to facilitate a visualization of a plurality of fields of view, e.g., at a plurality of angles with respect to the long axis of the endoscope by multiplexing image fields of view using an optical apparatus. In one exemplary embodiment of the present disclosure, an optical apparatus/system can be provided which can be partially reflective and/or may be a polarization or wavelength selective such that certain wavelengths or polarization states are directed to and/or received from different field angles and therefore illuminate and/or receive different fields of view.

The exemplary states may be altered by changing the characteristics of the optics or the optical characteristics of the light, such as the wavelengths or the polarization state. For example, such changes of wavelengths can be different bands of wavelengths in the RGB spectrum. Alternatively, the different wavelengths may be comprised of different wavelength bands in the visible and NIR spectrum. Furthermore, e.g., the characteristic(s) of the light is not changed by the optical apparatus, but the images are separated using software algorithms. In yet another embodiment, the optical apparatus contains a beam splitter. In a further exemplary embodiment of the present disclosure, the optical apparatus can be configured and/or structured to be within a cap that can be attached to the distal end of an endoscope, a catheter, a borescope, and/or a laparoscope device. For example, the cap can be disposable, and/or can contain one or more apertures or openings to allow the passage of devices, fluids, or tissue to effect a change in the anatomic structure.

According to another exemplary embodiment of the present disclosure, the arrangement of optical elements coupled with or to certain endoscopes, and exemplary signal processing methods can facilitate an acquisition of continuous multi-directional views, without the need for additional auxiliary imaging devices deployed through the endoscope accessory channel.

FIG. 1 shows a side cross-sectional block diagram of an imaging system/apparatus and optical elements thereof according to an exemplary embodiment of the present disclosure. For example, a distal imaging attachment cap 1 of the exemplary imaging system of FIG. 1 can be facilitated in an endoscope 14. The attachment cap 1 can contain an optical element/arrangement 4 which can include certain multiple configurations, such as but not limited to a fiber optic bundle, a tapered fiber optic bundle, a cone mirror, a partial cone mirror, a pentagon mirror, an inverted pyramid mirror, a prism, and/or multiple mobile optical elements. The use of such exemplary optical element/arrangement 4 can achieve, e.g., a side and retrograde endoscopic view while maintaining the endoscope's field of view 5, such as the forward field of view. The exemplary optical element 4 may also have or applied thereto a customized reflective material to facilitate a detailed and customized manipulation of the field of view or wavelengths. Such exemplary arrangement can facilitate the user of the exemplary endoscopic system to view both the forward field of view 5 and fields of view located to the side and retrograde 6 to the endoscope's objective lens 2 and endoscope light 3.

Figure 2:
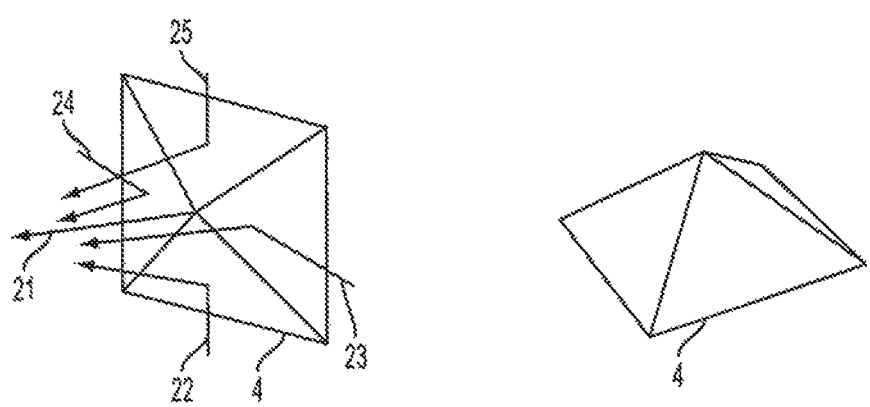
FIG. 2 is a set of view of an exemplary optical element consists a 4-faceted pyramid dichroic mirror which can transmit and reflect radiations with different characteristics according to an exemplary embodiment of the present disclosure.

According to another exemplary embodiment of the present disclosure, as shown in FIG. 2, the exemplary optical element 4 can be, e.g., a 4-faceted pyramid dichroic mirror which can transmit and/or reflect radiations (e.g., electromagnetic radiations, including light, etc.) with different characteristics. For example, the exemplary characteristics can include and/or be wavelengths or polarizations. The first and second radiations can have spectral regions in red, green and blue bands which likely do not substantially overlap with one another (at least for the most part). In addition or alternatively, the first and second radiations can have a specific polarization status. For example, the first radiation can be directed in a forward direction 21, and the second radiation can be directed in a backward direction or side directions (e.g., directions 22, 23, 24, 25).

Further, turning to FIG. 1, according to an exemplary embodiment of the present disclosure, it is possible to facilitate a toggling via a manual and/or electronic switch 8 (which can include a modulation arrangement), e.g., to apply an exemplary procedure to filter, polarize, bend and/or exclude predetermined wavelength(s) of one or more radiations (e.g., lights) 7 of an endoscopic light/radiation source 9. As indicated herein, the distal imaging attachment cap 1 can be placed at the distal tip of the endoscope 14.

Figure 3:
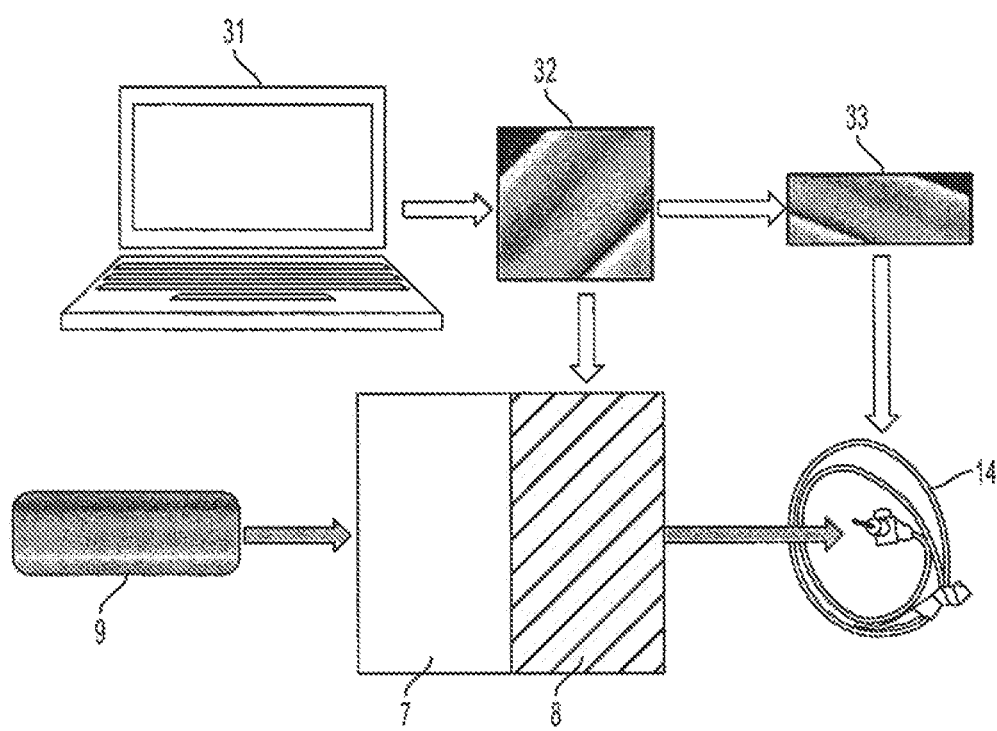
FIG. 3 a block diagram of an endoscopic arrangement, a radiation source arrangement, and a detector arrangement according to exemplary embodiments of the present disclosure.

According to another exemplary embodiment of the present disclosure, as shown in FIG. 3, a system can be provided (which can include but not limited to one or more of, e.g., computer 31, video capture device and synchronization signal generator 32, and endoscope video processor 33). The endoscopic arrangement 14 can be associated with the radiation source arrangement (which can include but not limited to one or more of, e.g., endoscopic light/radiation source 9, an exemplary procedure to filter, polarize, bend and/or exclude predetermined wavelength(s) of the radiation(s) 7, and manual and/or electronic switch 8) and a detector arrangement. Further, as indicated herein above, the radiation source arrangement can include the modulation arrangement (including, e.g., element 8) which can be configured to modulate the first and second radiations. The computer 31 and/or the signal generator 32 can be configured to synchronize the radiation source arrangement (including, e.g., elements 8, 9) and/or the entire system (including e.g., elements 31, 32, and 33). As an alternative or in addition, the computer 31 and/or the signal generator 32 can be configured to (i) synchronize the modulation arrangement (including, e.g., element 8) and the detector arrangement, and/or (ii) control the system to detect signals from the anatomical structure(s) illuminated by the first and second radiation, and separate the signals based the synchronization with the modulation arrangement (e.g., element 8).

Figure 4A:
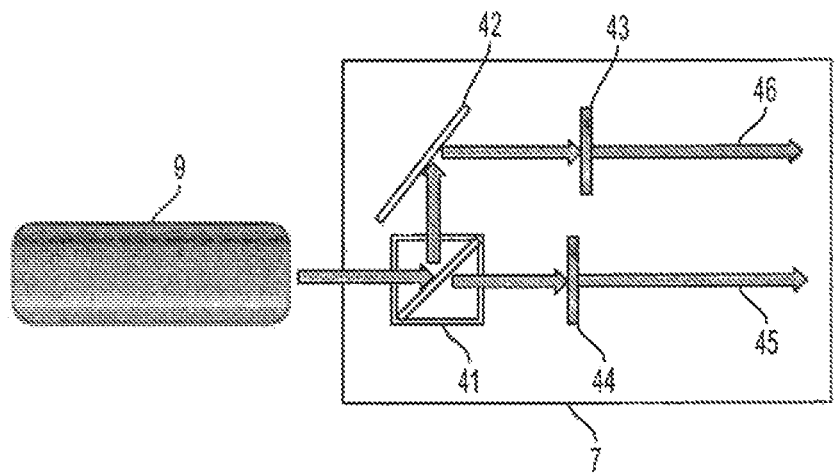
FIGS. 4(a) and 4(b) are block diagrams of exemplary modulation arrangements according to an exemplary embodiment of the present disclosure.

According to yet another exemplary embodiment of the present disclosure, as shown in FIG. 4(a), an exemplary modulation arrangement of another exemplary embodiment of the present disclosure can include a beam splitter 41 to divide the radiation (e.g., light and/or beam) into two beam paths. For example, one beam can pass a filter for predetermined wavelength(s) or polarization(s) 44 to provide the first radiation 45. The other beam can be reflected by a mirror 42, and can pass another filter for another predetermined wavelength(s) or polarization 43 with different characteristics compared with the wavelength(s) or polarization 44 to provide the second radiation 46.

Figure 4B:
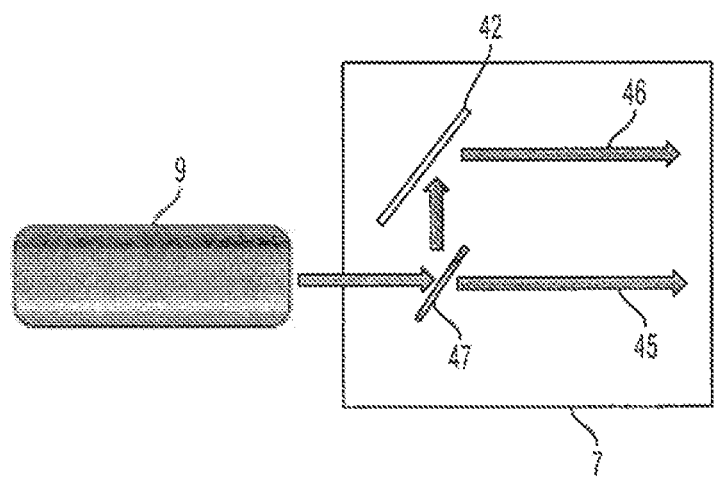

Further, as shown in FIG. 4(b), another exemplary modulation arrangement according to still another exemplary embodiment of the present disclosure can include a beam splitter for predetermined wavelength(s) or polarization 47 to provide the first radiation 45 and the second radiation 46.

Figure 5A:
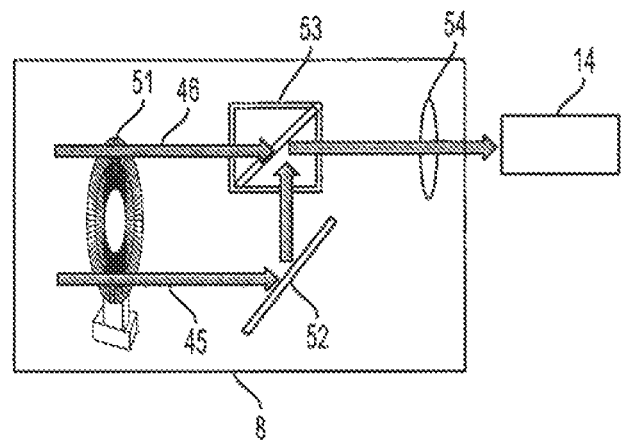
FIG. 5(a) is a diagram of an exemplary electronic switch based on an optical chopper according to an exemplary embodiment of the present disclosure.
Figure 5B:
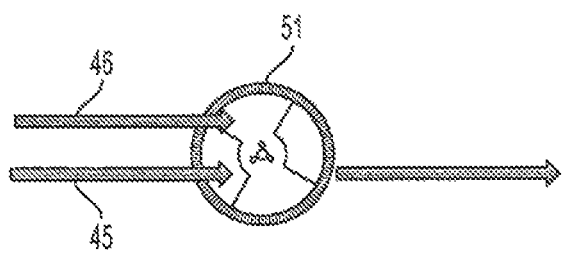
FIG. 5(b) is a diagram of the exemplary electronic switch based on a first switch position according to an exemplary embodiment of the present disclosure.
Figure 5C:
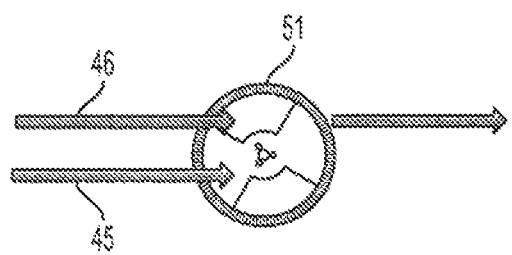
FIG. 5(c) is a diagram of the exemplary electronic switch based on a second switch position according to an exemplary embodiment of the present disclosure.

FIGS. 5(a)-5(c) illustrate block diagrams of various exemplary electronic switches according to further exemplary embodiments of the present disclosure. The exemplary electronic switches of FIGS. 5(a)-5(c) can include an optical chopper 51 synchronized with the computer 31 and/or the signal generator 32 (shown in FIG. 3). The first radiation 45 and second radiation 46 can be alternatively coupled into the endoscope 14 by exemplary optical components (e.g., a mirror 52, a beam splitter 53, and a lens 54). Such exemplary optical components can be switched by the optical chopper's positions, as shown in FIGS. 5(b) and 5(c).

Figure 6A:
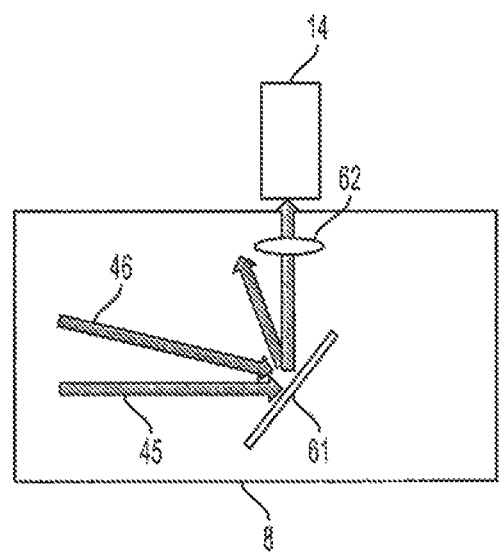
FIG. 6(a) a diagram of a further exemplary electronic switch based on a galvo scanner at a first switch position according to another exemplary embodiment of the present disclosure.
Figure 6B:
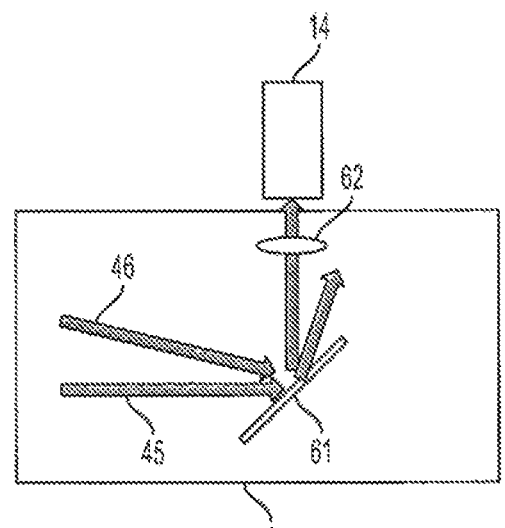
FIG. 6(b) a diagram of the exemplary electronic switch of FIG. 6(a) based on the galvo scanner at a second switch position according to another exemplary embodiment of the present disclosure.

FIGS. 6(a) and 6(b) show another exemplary electronic switch arrangement according to yet another exemplary embodiment of the present disclosure, provided in different switch position. The exemplary switch arrangement of FIGS. 6(a) and 6(b) can include a galvo scanner 61 which can be synchronized with the computer 31 and/or the signal generator 32 (shown in FIG. 3). For example, the first radiation 45 and the second radiation 46 can be alternatively coupled into the endoscope 14 by exemplary optical components (e.g., lens 62) switched by the galvo scanner's positions as shown in FIGS. 6(a) and 6(b).

Figure 7:
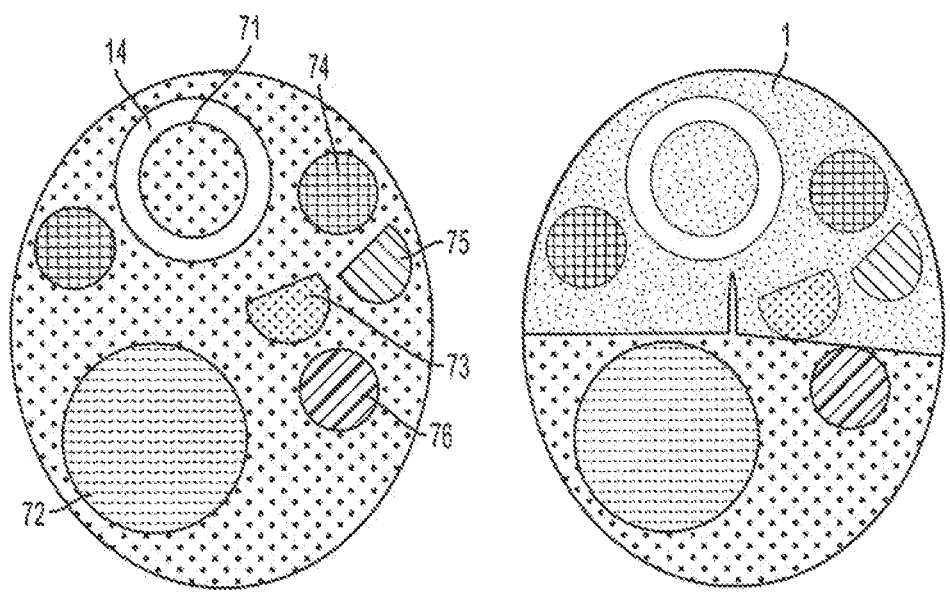
FIG. 7 a front view of the optical elements provided within a distal imaging attachment cap of the exemplary imaging system/apparatus of FIG. 1.

According to another exemplary embodiment of the present disclosure, as shown in FIG. 7, the exemplary distal imaging attachment cap 1 can facilitate a use of a fluid delivery channel 76 and/or an accessory channel 72 to maintain its original use by providing a non-obstructive pathway for an endoscopic manipulation within the endoscope 14 via the accessory channel 72. Other Exemplary Image Processing In one exemplary embodiment of the present disclosure, with reference to FIG. 1, the exemplary system/apparatus/method can be used for a simultaneous or controlled switching between the above described forward field of view 5 and the side/retrograde field of view 6. In order to facilitate accurate localization of target lesions obtained with the exemplary imaging system, an exemplary procedure 12 (which can be used to program a processing hardware arrangement, such as, e.g., a computer) can be used to deconstruct a wavelength/polarization "profile" of each field of view 10, 11 by electronically splitting native and multi-directional fields of view.

Using an a light/radiation source of the endoscope 14, exemplary selective filtering of, e.g., white light to facilitate only the reflectance or transmission phase to be analyzed can be accomplished by placing applying a filter at the endoscope's connection to its processing arrangement (e.g., the processor). Toggling between the on and off phases, e.g., manually (such as with a manual foot pedal), automatically or via an electronic switch, the reflected or transmitted light/radiation can then be deconstructed via a further procedure which can program or configure the processing arrangement to continuously display the forward and multidirectional fields of view 13.

According to yet further exemplary embodiment of the present disclosure, another procedure can be provided which can program or configure the processing arrangement to deconstruct each pixel, and display the two profiles determined by the reflective transmission wavelengths, polarizations or characteristic properties established by a special arrangement 7, the optical element(s) 4 and angles of observation of each field of view 5, 6.

Figure 8:
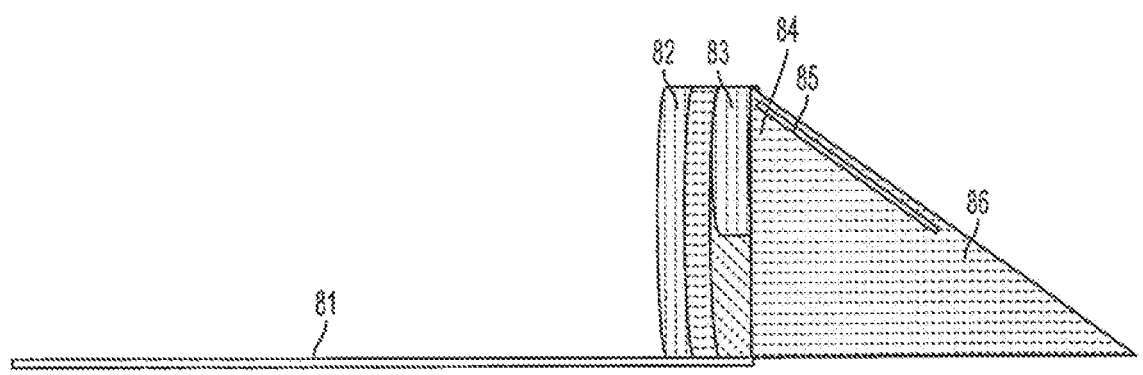
FIG. 8 a side view of the imaging system/apparatus, optical elements and distal imaging attachment cap, as shown in FIG. 7.

The exemplary imaging system of FIG. 1 can also use of an alternative light source which can be deployed, e.g., via the cap irrigation channel 81 (shown in FIG. 8). The use of such light source via the irrigation channel 81 can provide and/or facilitate, e.g., a further selective manipulation of the reflectance and transmission frequencies for an improved discretion between the phases for an exemplary image manipulation via a procedure which can program or configure the processing arrangement to perform such exemplary function.

Exemplary Application of Exemplary Embodiment

Exemplary Cap Design

According to one exemplary embodiment of the present disclosure, a plastic, transparent, semi-flexible disposable cap 1 can be fitted over the distal tip of the endoscope 14 via a friction fit configuration 82, as shown in FIG. 8. The exemplary design and/or configuration of this cap 1 can be provided in various ways, e.g., depending on the indication of the exemplary endoscopic procedure. Shapes of the exemplary cap 1 can include, but are not limited to oblique or perpendicular angled shapes, in respect to the distal aspect of the endoscope 14 and a location of the objective lens 2.

In a further exemplary embodiment of the present disclosure, the distal imaging attachment is designed to be in a specific orientation so as to facilitate the native functions of the endoscope to continue to operate without an interruption. To facilitate the function of, e.g., cleaning the endoscopes objective lens 71, a light guide 74, an air nozzle 73, and a water nozzle 75 (as shown in FIG. 7), the exemplary cap 1 can include a clearance chamber 83 (as shown in FIG. 8), which can seal the distal apparatus away from luminal liquid and contents, while continuing to facilitate the instillation of water for imaging and cleaning. This above described exemplary clearance chamber 83 can contain a perforation located above the accessory chamber 86 to facilitate suctioning of contents of the clearance chamber 83. To facilitate the distal imaging cap to be cleaned, a water jet output channel (e.g., the fluid delivery chamber) 76 can be provided which is structured and/or designed to be unobstructed by the exemplary cap 1. Furthermore, to provide more aggressive cleansing, e.g., the distal imaging cap is also structured and/or designed with an irrigator port 81 which can facilitate the attachment of a lavage device or syringe to aid in a clearance of liquid and/or debris from the distal attachment cap 1.

Further, the exemplary cap 1 can be coupled with multiple optical elements 85 in the optical chamber 84.

Overlapping Field Cap Design

Figure 9:
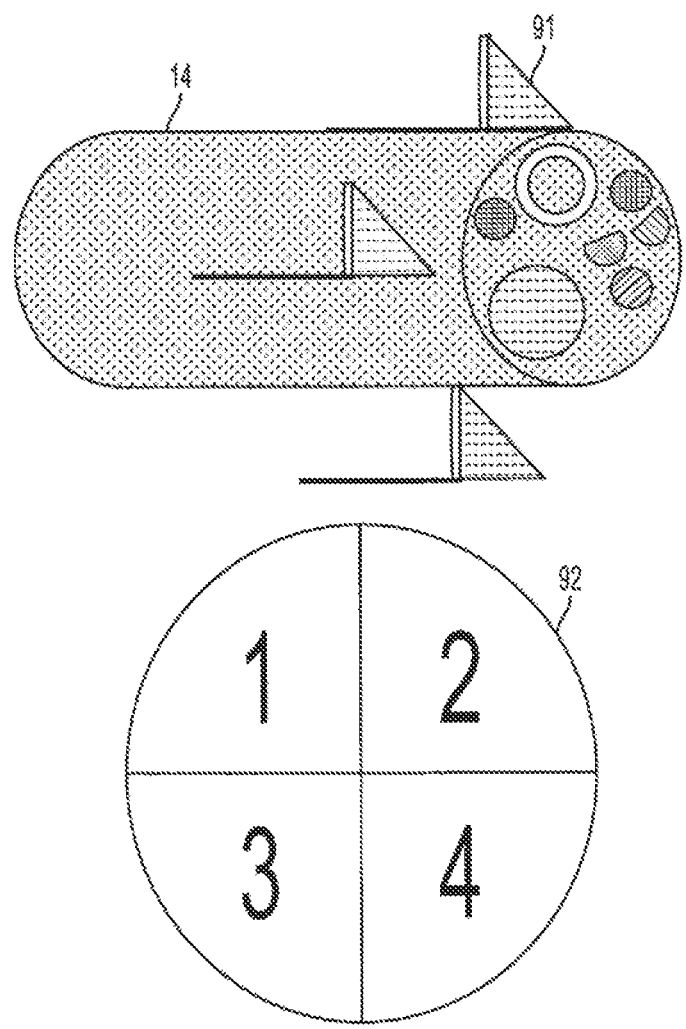
FIG. 9 is a set of illustrations providing external distal image attachments and an overlapping field external display Diagram according to exemplary embodiments of the present disclosure.

According to yet another exemplary embodiment of the present disclosure, it is possible to use a plastic, transparent, semi-flexible and disposable cap, which can facilitate a circular configuration and arrangement of multiple imaging detectors within a small collar 91, as shown in FIG. 9. This exemplary collar 91 can facilitate overlapping, multidirectional and circumferential views of the desired target sample (e.g., organ) or space being inspected. This exemplary configuration can facilitate the use of multiple light sources and independent optical sensors, e.g., bypassing a preference to alter the conventional endoscopes light source. Exemplary image processing of images obtained using the system, apparatus and method according to the present disclosure can be accomplished using the exemplary procedures implemented on the exemplary processing arrangement, as described herein. For example, depending on the number of optical elements placed within the exemplary imaging collar-cap design, an exemplary procedure implemented on the exemplary processing arrangement according to an exemplary embodiment of the present disclosure can assist in an alignment of the signals to provide, e.g., a 360 degree, multidirectional field of view 92, as shown in FIG. 9.

Exemplary Testing

Further exemplary testing was performed using the following: (1) Polka dot beam splitter, (2) 50:50 beam splitter AOI 45 degree, (3) long pass dichroic mirror, 50% Trans. Refl. At 567 nm, (4) cone mirror or (5) 395/495/610 nm Triple-edge dichroic beam splitter installed at multiple distances distal to the endoscopes objective leans. Preliminary testing with both a white light and infrared light source was successful in demonstrating that selective observation of the forward and retrograde views could be accomplished if the optical element was oriented at an angle such as a 45 degree, 30 degree, or 60 degree angle to the endoscopes objective lens.

Figure 10:
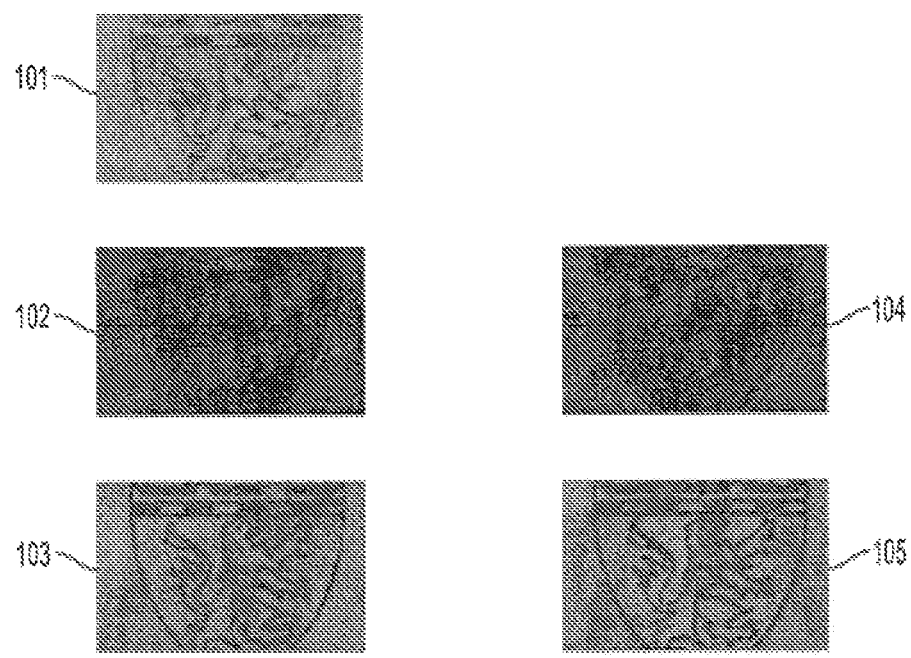
FIG. 10 is a set of exemplary images providing exemplary testing results achieved using the exemplary system, method and/or computer-accessible medium according to the exemplary embodiments of the present disclosure.

FIG. 10 shows a set of exemplary images achieved using the exemplary system, method and/or computer-accessible medium according to the exemplary embodiments of the present disclosure. Such exemplary images were based on exemplary testing result using an exemplary software separation via a simultaneously illumination and utilizing a 442/505/635 nm Yokogawa dichroic beamsplitter installed at the distal to a CCD camera with lens. Massachusetts General Hospital ("MGH") logo and Harvard Medical School ("HMS") logo were used as the image targets, placed in front of, and at side of the dichroic beamsplitter, respectively. In this testing, the white light source was not modulated and illuminated on the two image targets simultaneously. The separately captured exemplary individual images of the logos are shown in FIG. 10 as MGH 102, and HMS 103. A captured exemplary combined image 101 with the two logos in positions at the same time was the image intended to be processed. The exemplary procedure 12 described herein above with respect to FIG. 1 (which may be used to program a processing hardware arrangement, such as, e.g., a computer) can be utilized to deconstruct the wavelength "profile" of each field of view by splitting the native and multidirectional fields of view with the two logos. For example, the exemplary procedure 12 can be one or more programs including, but not limited to, e.g., Neural Network and/or Independent Component Analysis, or other procedure/program which can configure the processing hardware arrangement to separate the two views from the captured combined image 101. The exemplary reconstructed images of each field of view are shown in FIG. 10 as images 104, 105, respectively. The exemplary software based separation, which splits the two views as described herein, can significantly reduce the complexity of various components/parts of the procedure, system and computer-accessible medium according to the exemplary embodiments of the present disclosure.

An exemplary integration of such exemplary configuration that is associated with a distal imaging cap which is coupled with various optical elements has been described herein.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

EXEMPLARY REFERENCES

1. Winawer S J, Zauber A G, Ho M N, O'Brien M J, Gottlieb L S, Sternberg S S, Waye J D, Schapiro M, Bond J H, Panish J F, et al. Prevention of colorectal cancer by colonoscopic polypectomy. The National Polyp Study Workgroup. N Engl J Med 1992; 329:1977-81.
2. Bressler B, Paszat L F, Vinden C, Li C, He J, Rabeneck L. Colonoscopic miss rates for right-sided colon cancer: a population-based analysis. Gastroenterology 2004; 127: 452-6.
3. Rex D K, Cutler C S, Lemmel G T, Rahmani E Y, Clark D W, Helper D J, Lehman G A, Mark D G. Colonoscopic miss rates of adenomas determined by back-to-back colonoscopies. Gastroenterology 1997; 112:24-8.
4. Haseman J H, Lemmel G T, Rahmani E Y, Rex D K. Failure of colonoscopy to detect colorectal cancer: evaluation of 47 cases in 20 hospitals. Gastrointest Endosc 1997; 45:451-5.
5. Pellise M, Fernandez-Esparrach G, Cardenas A, Sendino O, Ricart E, Vaquero E, Gimeno-Garcia A Z, de Miguel C R, Zabalza M, Gines A, Pique J M, Llach J, Castells A. Impact of wide-angle, high-definition endoscopy in the diagnosis of colorectal neoplasia: a randomized controlled trial. Gastroenterology 2008; 135:1062-8.
6. Rex D K, Chadalawada V, Helper D J. Wide angle colonoscopy with a prototype instrument: impact on miss rates and efficiency as determined by back-to-back colonoscopies. Am J Gastroenterol 2003; 98:2000-5.
7. Deenadayalu V P, Chadalawada V, Rex D K. 170 degrees wide-angle colonoscope: effect on efficiency and miss rates. Am J Gastroenterol 2004; 99:2138-42.
8. Matsushita M, Hajiro K, Okazaki K, Takakuwa H, Tominaga M. Efficacy of total colonoscopy with a transparent cap in comparison with colonoscopy without the cap. Endoscopy 1998; 30:444-7.
9. Lee Y T, Hui A J, Wong V W, Hung L C, Sung J J. Improved colonoscopy success rate with a distally attached mucosectomy cap. Endoscopy 2006; 38:739-42.
10. Kondo S, Yamaji Y, Watabe H, Yamada A, Sugimoto T, Ohta M, Ogura K, Okamoto M, Yoshida H, Kawabe T, Omata M. A randomized controlled trial evaluating the usefulness of a transparent hood attached to the tip of the colonoscope. Am J Gastroenterol 2007; 102:75-81.
11. Harada Y, Hirasawa D, Fujita N, Noda Y, Kobayashi G, Ishida K, Yonechi M, Ito K, Suzuki T, Sugawara T, Horaguchi J, Takasawa O, Obana T, Oohira T, Onochi K, Kanno Y, Kuroha M, Iwai W. Impact of a transparent hood on the performance of total colonoscopy: a randomized controlled trial. Gastrointest Endose 2009; 69:637-44.
12. Horiuchi A, Nakayama Y. Improved colorectal adenoma detection with a transparent retractable extension device. Am J Gastroenterol 2008; 103:341-5.
13. Hewett D G, Rex D K. Cap-fitted colonoscopy: a randomized, tandem colonoscopy study of adenoma miss rates. Gastrointest Endose 2010; 72:775-81.
14. Triadafilopoulos G, Watts H D, Higgins J, Van Dam J. A novel retrograde-viewing auxiliary imaging device (Third Eye Retroscope) improves the detection of simulated polyps in anatomic models of the colon. Gastrointest Endosc 2007; 65:139-44.
15. Leufkens A M, DeMarco D C, Rastogi A, Akerman P A, Azouzi K, Rothstein R I, Vleggaar F P, Repici A, Rando G, Okolo P I, Dewit O, Ignjatovic A, Odstrcil E, East J, Deprez P H, Saunders B P, Kalloo A N, Creel B, Singh V, Lennon A M, Siersema P D. Effect of a retrograde-viewing device on adenoma detection rate during colonoscopy: the TERRACE study. Gastrointest Endosc 2011; 73:480-9.

What is claimed is:

1. An apparatus for imaging at least one anatomical structure, comprising:
   an imaging probe first arrangement;
   a radiation source second arrangement provides at least one electro-magnetic radiation;
   a third arrangement attached to at least one portion of the first arrangement, and containing an optical arrangement which, upon impact by the at least one electro-magnetic radiation and based thereon, transmits a first radiation and reflects a second radiation, wherein the first radiation impacts at least one first portion of the at least one anatomical structure, and the second radiation impacts at least one second portion of the at least one anatomical structure, the first and second portions being at least partially different from one another;
   a detector arrangement, wherein the imaging probe first arrangement is associated with the radiation source second arrangement and the detector arrangement; and
   an electronic arrangement which is configured to synchronize the radiation source second arrangement and the detector arrangement,
   wherein the optical arrangement causes the first and second radiations to have characteristics which are different from one another,
   wherein the first radiation is directed in a forward direction, and wherein the second radiation is directed in a direction that is different from the forward direction, and
   wherein the radiation source second arrangement includes a modulation arrangement which is configured to alternate the first and second radiations.

2. The apparatus according to claim 1, wherein the characteristics are wavelengths or polarizations.

3. The apparatus according to claim 1, wherein the first and second radiations have spectral regions in red, green and blue band which do not substantially overlap with one another.

4. The apparatus according to claim 1, wherein the second radiation is directed in a backward direction or a side direction.

5. The apparatus according to claim 4, wherein the optical arrangement causes the second radiation to simultaneously illuminate between 270 and 360 degrees of a field of view with respect to a longitudinal axis of a probe.

6. The apparatus according to claim 1, wherein the third arrangement includes a cap that is connected to an end portion of the first arrangement.

7. The apparatus according to claim 1, wherein the electronic arrangement which is configured (i) synchronize the modulation arrangement and the detector arrangement, and (ii) control the detector arrangement to detect signals from the at least one anatomical structure illuminated by the first and second radiations, and separate the signals based the synchronization with the modulation arrangement.

8. The apparatus according to claim 1, wherein the at least one anatomical structure is a luminal anatomical structure.

9. The apparatus according to claim 1, wherein the third arrangement includes at least one opening which facilitates a passage of instrumentation, air gasses and fluids therethrough.

10. The apparatus according to claim 1, further comprising a tube associated with the third arrangement, and provides a passage of instrumentation, air gasses and fluids therethrough.

11. The apparatus according to claim 1, wherein the first and second radiations have a specific polarization status.

* * * * *